(12) United States Patent
Koike

(10) Patent No.: US 8,329,102 B2
(45) Date of Patent: *Dec. 11, 2012

(54) CONVEYING DEVICE AND SAMPLE PROCESSING METHOD

(75) Inventor: Hiroki Koike, Kobe (JP)

(73) Assignee: Sysmex Corporation, Hyogo (JP)

( * ) Notice: Subject to any disclaimer, the term of this patent is extended or adjusted under 35 U.S.C. 154(b) by 439 days.

This patent is subject to a terminal disclaimer.

(21) Appl. No.: 11/389,312

(22) Filed: Mar. 27, 2006

(65) Prior Publication Data

US 2006/0216199 A1   Sep. 28, 2006

(30) Foreign Application Priority Data

Mar. 28, 2005   (JP) ................. 2005-091060

(51) Int. Cl.
| G01N 21/00 | (2006.01) |
| G01N 31/00 | (2006.01) |
| G01N 33/00 | (2006.01) |
| B65G 47/10 | (2006.01) |
| B65G 47/46 | (2006.01) |
| B65G 35/00 | (2006.01) |

(52) U.S. Cl. ............. 422/65; 198/348; 198/618
(58) Field of Classification Search ........ 436/47; 422/65; 198/358

See application file for complete search history.

(56) References Cited

U.S. PATENT DOCUMENTS

| 3,724,638 | A | * | 4/1973 | Peters et al. ............ 198/464.2 |
| 5,209,903 | A | | 5/1993 | Kanamori et al. |
| 5,232,081 | A | | 8/1993 | Kanamori |
| 5,529,166 | A | * | 6/1996 | Markin et al. ............ 198/349 |
| 5,972,295 | A | * | 10/1999 | Hanawa et al. ............ 422/65 |
| 6,345,925 | B1 | * | 2/2002 | Coleman .............. 403/24 |
| 6,444,171 | B1 | * | 9/2002 | Sakazume et al. .......... 422/65 |
| 6,571,934 | B1 | * | 6/2003 | Thompson et al. ......... 198/619 |
| 6,808,304 | B2 | * | 10/2004 | Gebrian et al. ............ 366/110 |
| 7,448,487 | B2 | * | 11/2008 | Koike .............. 198/358 |
| 2004/0042339 | A1 | * | 3/2004 | Gebrian et al. ............ 366/208 |
| 2005/0031492 | A1 | * | 2/2005 | Koike .............. 422/82.01 |

FOREIGN PATENT DOCUMENTS

| JP | 9-43246 A | 2/1997 |
| JP | 2000-105248 A | 4/2000 |

* cited by examiner

*Primary Examiner* — Sam P Siefke
*Assistant Examiner* — Bryan Kilpatrick
(74) *Attorney, Agent, or Firm* — Sughrue Mion, PLLC

(57) ABSTRACT

A conveying device, intended for use in conveying a rack, which holds a sample container, to a sample supplying position for supplying a sample in the sample container to a sample processing device for processing the sample, comprising a conveying section for conveying the rack in a conveying direction from a predetermined position on the conveying device to the sample supplying position along a path connecting the predetermined position and the sample supplying position, wherein the conveying section is adapted to convey the rack from the sample supplying position in a direction opposite to the conveying direction, is disclosed. A sample processing method is also disclosed.

18 Claims, 49 Drawing Sheets

CONVEYING DEVICE AND SAMPLE PROCESSING METHOD

FIELD OF THE INVENTION

This invention relates to a conveying device for conveying a rack on which a sample container is held to a sample supplying position for supplying a sample in the sample container to a sample processing device for processing the sample, and sample processing method for processing a sample using the conveying device.

BACKGROUND

Hitherto, a conveying device is known which conveys a rack on which a sample container is held to a sample supplying position for supplying a sample to a sampler processing device for processing the sample (refer to, for example, Japanese Patent Laid-Open (JP-A) No. Hei 9-43246). The sample processed by the processing device is contained in a sample container held on the rack. JP-A No. H9-43246 discloses a conveying device having a buffer, a first feeder, and a second feeder.

In the conveying device disclosed in JP-A No. H9-43246, the buffer has the functions of storing a rack introduced from an introduction port of the conveying device and conveying the stored rack to the first feeder. The first feeder has the function of conveying the rack conveyed from the buffer to a sample supplying position and the second feeder. The second feeder has the function of carrying out the rack conveyed by the first feeder to the outside from an outlet of the conveying device. The buffer, the first feeder, and the second feeder can convey the racks only in one direction. Concretely, the racks conveyed from the buffer are moved only toward the first feeder side. The racks conveyed from the first feeder are moved only in a direction toward the sample supplying position (second feeder). The racks conveyed by the second feeder are moved only in a direction toward the outlet of the conveying device.

When an error occurs in the sample processing device during process of a predetermined sample in the conventional conveying device, in order to re-process the predetermined sample in the same sample processing device, a predetermined rack on which a sample container containing the pre-determined sample is held is re-stored in the buffer, and the predetermined rack has to be conveyed again to the sample supplying position by the first feeder. In this case, since the conveying device of JP-A No. H9-43246 is constructed so that the racks are conveyed only in one direction in the buffer, there is an inconvenience such that the user has to move racks already stored in order to assure a space for re-storing the predetermined rack. The technique of JP-A No. H9-43246 has a drawback that the burden on the user is heavy at the time of re-processing a sample in the same sample processing device.

SUMMARY

The scope of the present invention is defined solely by the appended claims, and is not affected to any degree by the statements within this summary.

A first aspect of the present invention is a conveying device, intended for use in conveying a rack, which holds a sample container, to a sample supplying position for supplying a sample in the sample container to a sample processing device for processing the sample, comprising:

a conveying section for conveying the rack in a conveying direction from a predetermined position on the conveying device to the sample supplying position along a path connecting the predetermined position and the sample supplying position;

wherein the conveying section is adapted to convey the rack from the sample supplying position in a direction opposite to the conveying direction.

A second aspect of the present invention is a conveying device, intended for use in conveying racks, which hold sample containers to a sample supplying position for supplying a sample in the sample container to a sample processing device for processing the sample, comprising:

a conveying mechanism for conveying the racks forward to the sample supplying position one by one; and a space maker for making a space for at least one rack, on the conveying device, to receive a rearward-moving rack.

A third aspect of the present invention is a sample processing method for processing a sample, comprising:

(a) conveying a sample forward to a sample supplying position;

(b) processing the sample with a sample processing device;

(c) in response to a reprocessing command, conveying the sample rearward; and (d) again conveying the sample forward to the sample supplying position for reprocessing.

DETAILED DESCRIPTION OF THE PREFERRED EMBODIMENTS

The preferred embodiments of the present invention are described hereinafter with reference to the drawings.

First Embodiment

Figure 2:
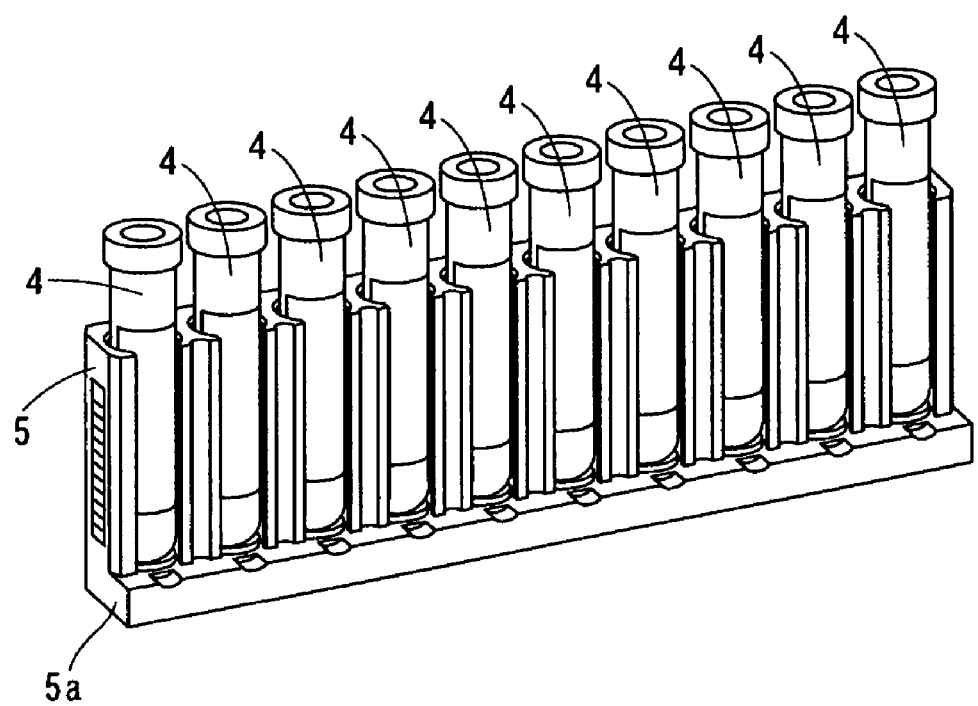
FIGS. 2 and 3 are perspective views each showing the structure of a rack conveyed by the conveying device according to the first embodiment shown in FIG. 1.
Figure 3:
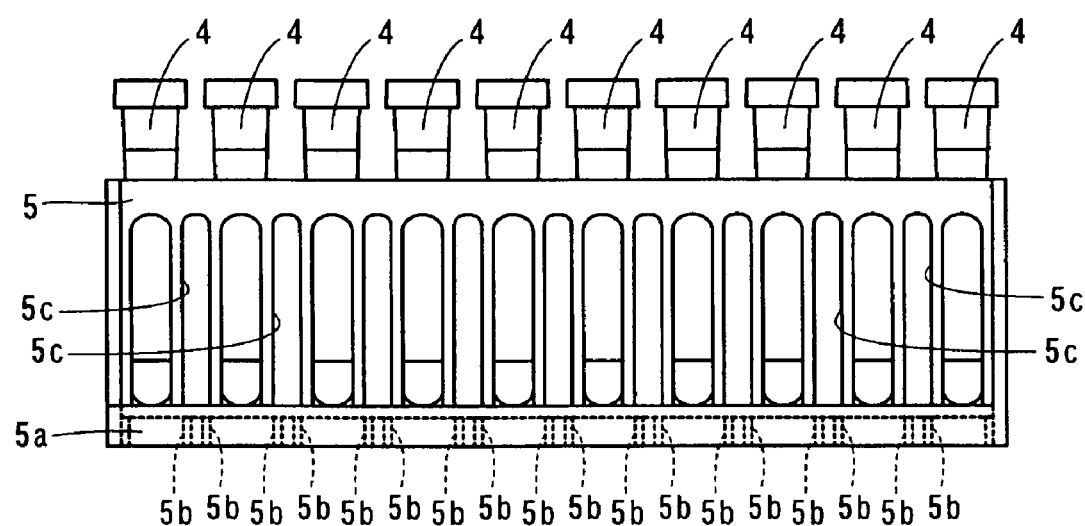

A sample processing system including a first blood analyzer 2 and a second blood analyzer 3 to each of which a conveying device 1 according to the first embodiment is connected will be described with reference to FIGS. 1 to 3.

Figure 1:
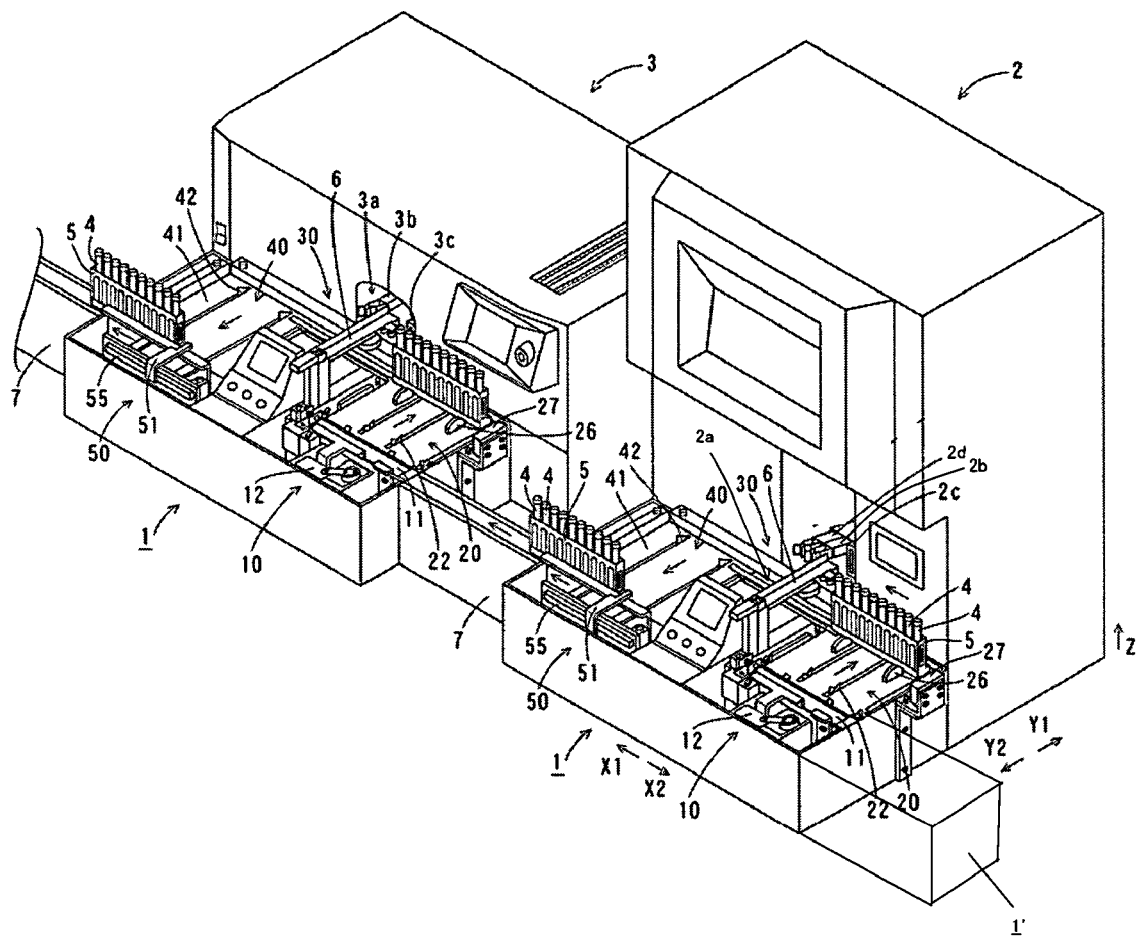
FIG. 1 is a perspective view showing a state where a conveying device according to a first embodiment of the invention is connected to an analyzer.

Two conveying devices 1 according to the first embodiment are connected to, for example, as shown in FIG. 1, the first blood analyzer 2 for conducting a primary analysis and the second blood analyzer 3 for conducting a secondary analysis. The primary analysis by the first blood analyzer 2 is conducted on all of samples, and the secondary analysis by the second blood analyzer 3 is conducted on only samples determined to be subjected to a detailed analysis on the basis of the result of the primary analysis. Both of the first and second blood analyzers 2 and 3 are devices for processing blood. The first blood analyzer 2 is a hemacytometer, and the second blood analyzer 3 is a blood smear preparing device.

The conveying device 1 connected to the first blood analyzer 2 is disposed adjacent to a conveying device 1', and receives a rack conveyed from the conveying device 1'.

Samples are contained in sample containers 4 which are held on a rack 5. The rack 5 can hold 10 sample containers 4 as shown in FIGS. 2 and 3. The rack 5 has a bottom 5a which is longer in shorter direction than the part in which the sample containers 4 are housed. A space area is provided on the back side of the rack 5 and a plurality of plates 5b are provided in the space area on the back side of the rack 5. On the side of a part in which the sample containers 4 are housed of the rack 5, a plurality of slots 5c are provided.

As shown in FIG. 1, the conveying device 1 has the function of conveying the rack 5 on which the sample containers 4 are held to a sample supplying position 2a for supplying the samples to the first blood analyzer 2 and a sample supplying position 3a for supplying the samples to the second blood analyzer 3. The first blood analyzer 2 has a hand member 2b for taking the sample container 4 from the rack 5 and stirring the sample in the sample container 4. The first blood analyzer 2 also has, in a position opposite to the sample supplying position 2a, a hand member 2d for taking the sample container 4 from the rack 5 and supplying the sample into the first blood analyzer 2.

On the other hand, the second blood analyzer 3 has, in a position opposite to the sample supplying position 3a, a hand member 3b for taking a sample container 4 from the rack 5, stirring the sample in the sample container 4, and supplying the sample into the second blood analyzer 3.

In the first and second blood analyzers 2 and 3, barcode readers 2c and 3c for reading a barcode adhered to a sample container 4 are disposed, respectively. The barcode readers 2c and 3c are connected to the conveying devices 1 via not-shown cables and operate on the basis of instructions from the conveying device 1.

In a position opposite to each of the barcode readers 2c and 3c, on the conveying device 1, a sample container turning device 6 for turning the sample containers 4 held on the rack 5 is disposed. A barcode adhered to the sample container 4 is read by the barcode readers 2c and 3c while turning the sample container 4 by the sample container turning device 6.

The two conveying devices 1 are connected to each other via an intermediate conveying device 7. The two conveying devices 1 have the same structure.

The structure of the conveying device 1 will now be described in detail with reference to FIGS. 4 to 19.

Figure 4:
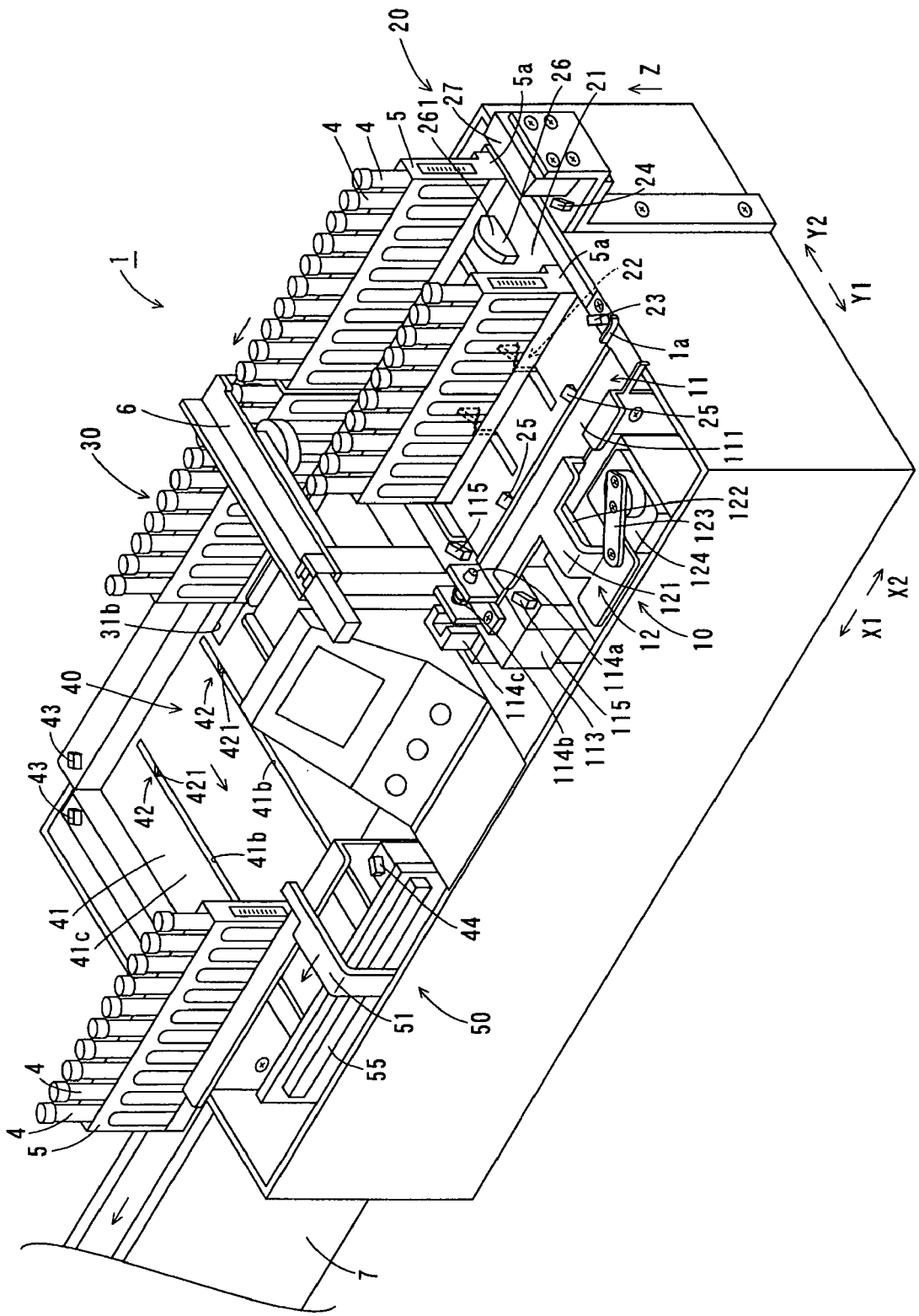
FIG. 4 is a perspective view showing the structure of the conveying device according to the first embodiment of the invention.
Figure 5:
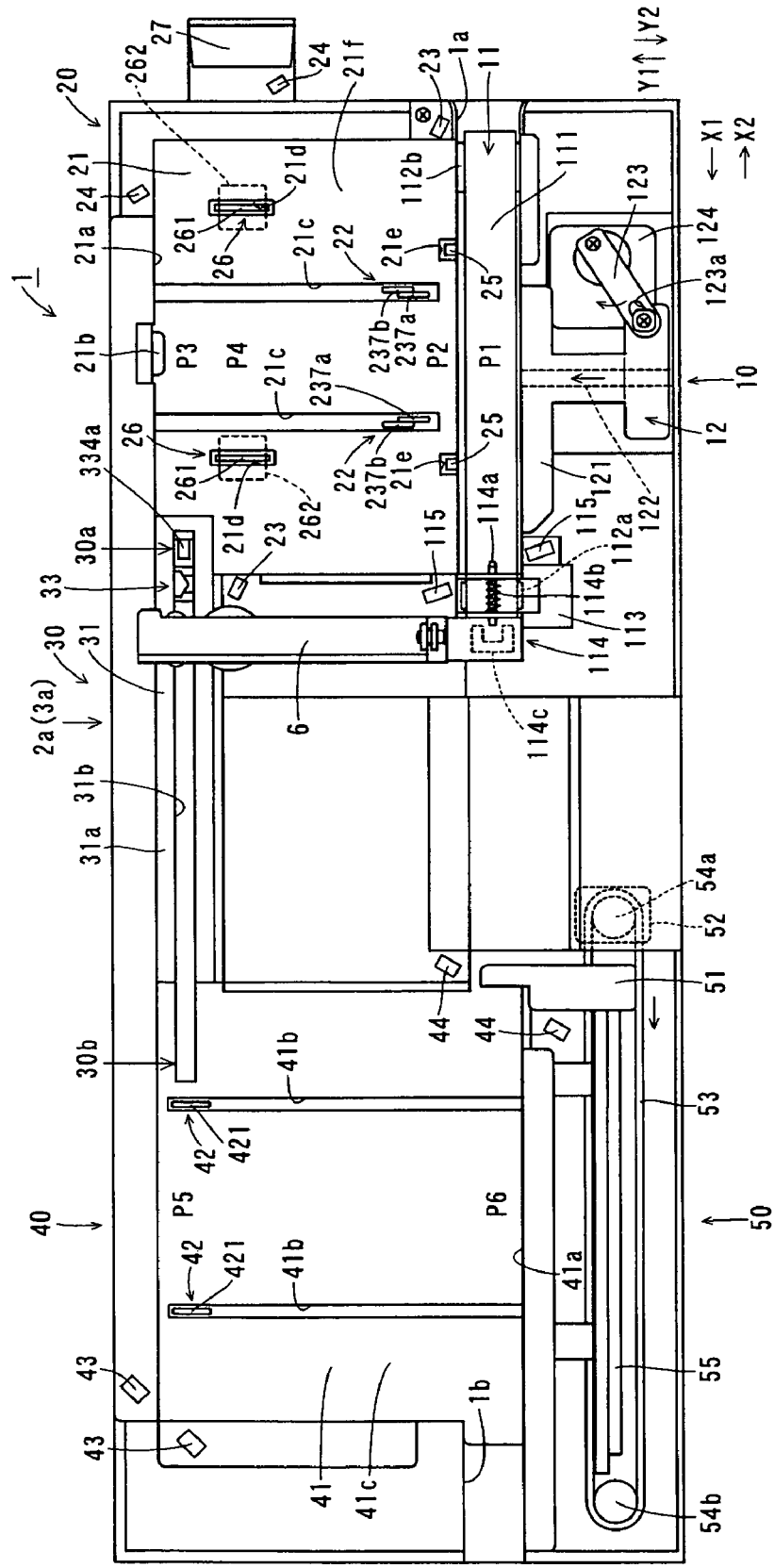
FIG. 5 is a plan view showing the structure of the conveying device according to the first embodiment of the invention.

The conveying device 1 has, as shown in FIGS. 4 and 5, a rack receiver 10, a storing section 20, a conveying section 30, a carrying-out section 40, and an unloading section 50.

The rack receiver 10 in the conveying device 1 is provided to move the rack 5 introduced from an inlet 1a of the conveying device 1 in the X1 direction and, after that, push the rack 5 to the storing section 20. The rack receiver 10 includes a rack loading mechanism 11 and a rack pushing mechanism 12.

The rack loading mechanism 11 of the rack receiver 10 is provided to move the rack 5 introduced from the inlet 1a in the X1 direction. The rack loading mechanism 11 includes a conveyance belt 111, pulleys 112a and 112b, a motor 113, a detector 114, and a transmission sensor 115. The conveyance belt 111 is attached to the pulleys 112a and 112b, and the pulley 112a is coupled to the motor 113. Consequently, by driving the motor 113, the conveyance belt 111 is driven via the pulley 112a. In the case where the rack 5 is introduced from the inlet 1a, by driving the conveyance belt 111 in the X1 direction, the rack 5 is moved in the X1 direction.

The detector 114 of the rack loading mechanism 11 is provided to detect that the rack 5 moved in the X1 direction by the conveyance belt 111 arrives at a push position P1. The push position P1 is a position in which the rack 5 can be pushed to the storing section 20 side by the rack pushing mechanism 12. The detector 114 has a detection pin 114a, a compression spring 114b, and a transmission sensor 114c. The detection pin 114a is energized by the compression spring 114b so that one end projects toward the push position P1. The transmission sensor 114c is disposed at the other end of the detection pin 114a. In the case where the rack 5 is conveyed to the push position P1 by the conveyance belt 111, one end of the detection pin 114a is pressed against the rack 5, thereby moving the detection pin 114a in the X1 direction against the energizing force of the compression spring 114b. Since the transmission sensor 114c enters a light shield state due to the other end of the detection pin 114a, arrival at the push position P1 of the rack 5 moved in the X1 direction by the conveyance belt 111 is detected.

The transmission sensor 115 of the rack loading mechanism 11 is provided to detect the presence/absence of the rack 5 in the push position P1 and to detect that the rack 5 is pushed from the push position P1 to the storing section 20 side by the rack pushing mechanism 12. The transmission sensor 115 is disposed so as to enter a light shield state when the rack 5 exists in the push position P1.

The rack pushing mechanism 12 of the rack receiver 10 is provided to push the rack 5 conveyed to the push position P1 to the storing section 20 side. The rack pushing mechanism 12 is constructed by a pushing member 121, a direct-drive guide 122, an arm 123, and a motor 124. The pushing member 121 is attached to the direct-drive guide 122, and the direct-drive guide 122 is disposed so as to extend in the Y1 direction (Y2 direction). A long hole 123a is formed in one end of the arm 123. The one end of the arm 123 is attached to the pushing member 121 via the long hole 123a, and the other end is coupled to the rotary shaft of the motor 124. With the configuration, when the motor 124 is driven, one end of the arm 123 swings and the pushing member 121 is moved along the extending direction (Y1 direction) of the direct-drive guide 122. Therefore, in the case where the rack 5 exists in the push position P1, the rack 5 can be pushed to the storing section 20 side by the pushing member 121.

The storing section 20 in the conveying device 1 is provided to store the rack 5 conveyed from the inlet 1a to the sample supplying position 2a (3a). Further, in the first embodiment, the storing section 20 also has the function of re-storing the rack 5 moved in the direction opposite to the conveyance direction from the sample supplying position 2a (3a) in the case where a re-analysis is conducted. The storing section 20 includes a storage plate 21, a first rack moving mechanism 22, transmission sensors 23 and 24, a reversal preventing member 25, a storage regulating mechanism 26, and a barcode reader 27.

The storage plate 21 in the storing section 20 has a rack contact part 21a, a storage regulating part 21b, a pair of holes 21c, a pair of holes 21d, and notches 21e. The rack contact part 21a is provided on the side opposite to the rack receiver 10 side of the storage plate 21. The rack contact part 21a is formed by bending the storage plate 21 in the direction perpendicular to a mounting surface 21f. An area between the end (reversal preventing member 25) on the rack receiver 10 side of the storage plate 21 and the rack contact part 21a is a storage area in which the rack can be stored. An area of the size of one rack 5 at the end on the rack receiver 10 side of the storage plate 21 is a rack receive position P2 for receiving the rack 5 pushed from the rack receiver 10. An area of the size of one rack 5 on the rack contact part 21a side of the storage plate 21 is a transverse feed start position P3 in which conveyance of the rack 5 by the conveying section 30 starts.

Figure 6:
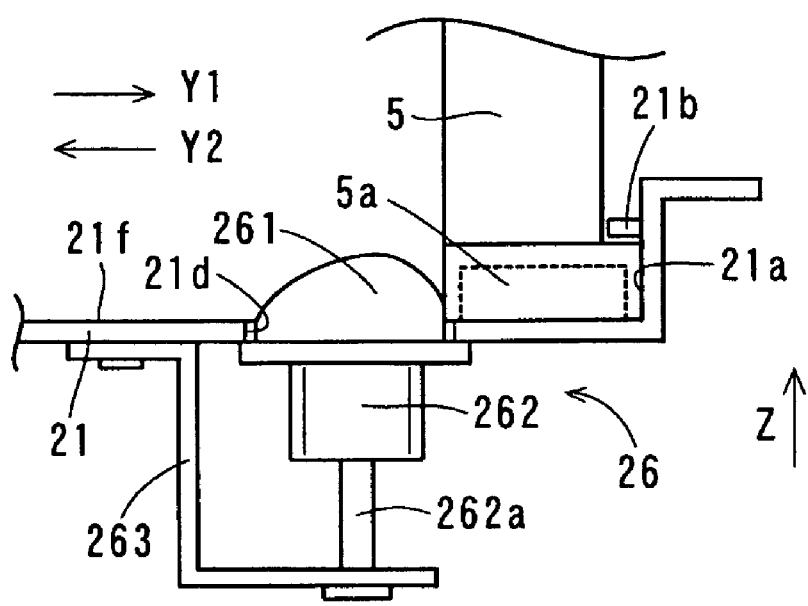
FIG. 6 is a side view showing the structure of the periphery of a storage regulating mechanism in the conveying device according to the first embodiment illustrated in FIGS. 4 and 5.

The storage regulation part 21b of the storage plate 21 is formed by bending a predetermined area in the rack contact part 21a so as to be parallel to the mounting surface 21f. The storage regulating part 21b is formed so as to project to the transverse feed start position P3 side from the rack contact part 21a. The storage regulating part 21b is provided so that the user cannot put the rack 5 in the transverse feed start position P3. As shown in FIG. 6, the distance from the mounting surface 21f of the storage regulating part 21b is set to be smaller than the general height of the rack 5 and larger than the height of the bottom 5a of the rack 5. The projection amount from the rack contact part 21a of the storage regulating part 21b is set so that, when the rack 5 (bottom 5a) comes into contact with the rack contact part 21a, the rack 5 does not come into contact with the storage regulating part 21b.

As shown in FIGS. 4 and 5, the pair of holes 21c in the storage plate 21 is formed so as to extend from the rack receive position P2 to the transverse feed start position P3 in the storage plate 21. The pair of holes 21d in the storage plate 21 is formed in a rectangle shape so as to have a length in the longer direction substantially the same as the length in the shorter direction of the rack 5 (bottom 5a). The pair of holes 21d in the storage plate 21 is disposed in areas apart from the rack contact part 21a by a distance which is substantially the same as the length in the shorter direction of the rack 5 (bottom 5a) so as to sandwich the pair of holes 21c. The area in which the pair of holes 21d is formed in the storage plate 21 is the area (reserve storage position P4) in which storage of the rack 5 is regulated. The pair of notches 21e in the storage plate 21 is formed at an end on the rack receiver 10 side of the storage plate 21.

Figure 7:
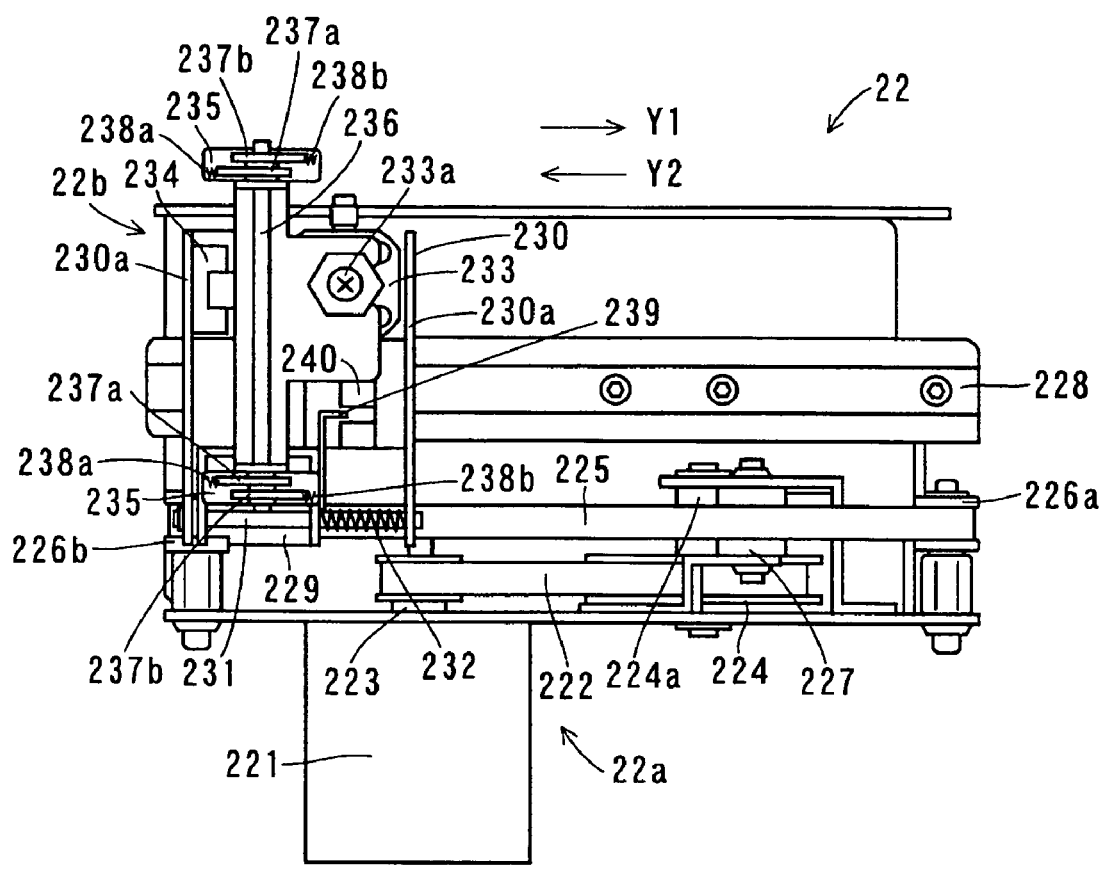
FIG. 7 is a plan view showing the structure of a first rack moving mechanism in the conveying device according to the first embodiment illustrated in FIGS. 4 and 5.
Figure 8:
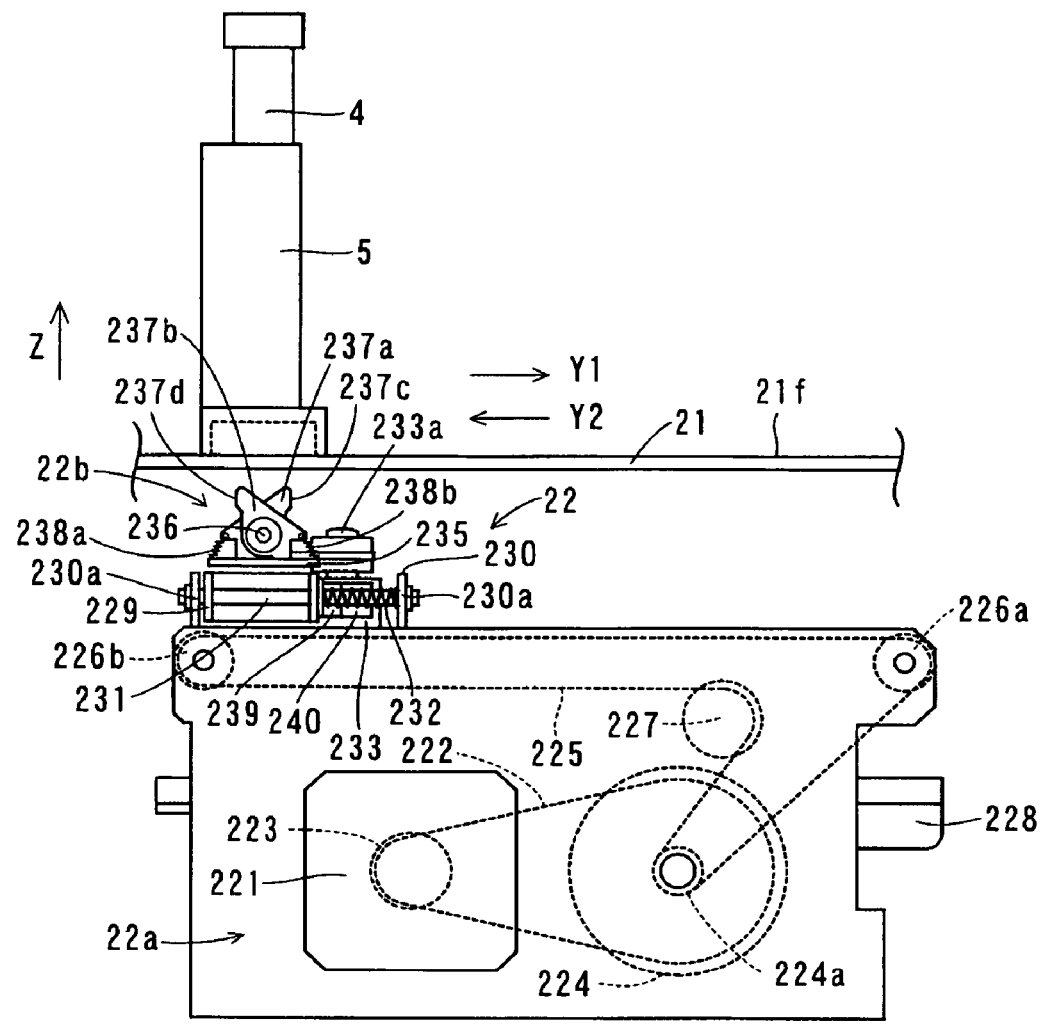
FIG. 8 is a side view of the first rack moving mechanism shown in FIG. 7.

In the first embodiment, the first rack moving mechanism 22 in the storing section 20 has the function of moving the rack 5 stored on the mounting surface 21f of the storage plate 21 from the rack receive position P2 side to the transverse feed start position P3 side (Y1 direction) and, in addition, the function of moving the rack 5 in the direction opposite to the conveying direction from the transverse feed start position P3 side to the rack receive position P2 side (Y2 direction). The first rack moving mechanism 22 is constructed by, as shown in FIGS. 7 and 8, a driving unit 22a and a rack conveying unit 22b. The driving unit 22a is provided to move the rack conveying unit 22b in the Y1 direction (conveyance direction) and the Y2 direction (the direction opposite to the conveyance direction) and is disposed below the mounting surface 21f of the storage plate 21. The driving unit 22a has a motor 221, an intermediate belt 222, a motor pulley 223, a large-diameter pulley 224, a drive belt 225, pulleys 226a and 226b, a tension pulley 227, and a direct-drive guide 228. The intermediate belt 222 is attached to the motor pulley 223 and the large-diameter pulley 224, and the motor pulley 223 is coupled to the motor 221. The drive belt 225 is attached to the pulleys 226a and 226b, and a small-diameter part 224a of the large-diameter pulley 224. Tension is given to the drive belt 225 by the tension pulley 227. Consequently, by the driving of the motor 221, the drive belt 225 is decelerated and driven via the intermediate belt 222, motor pulley 223, and large-diameter pulley 224. The direct-drive guide 228 is disposed so as to extend in the Y1 direction (Y2 direction).

In the first embodiment, the rack conveying unit 22b of the first rack moving mechanism 22 is provided to move the rack 5 stored on the mounting surface 21f of the storage plate 21 in the Y1 and Y2 directions. The rack conveying unit 22b includes a first moving member 229 and a second moving member 230. The first moving member 229 is coupled to the drive belt 225, and the second moving member 230 is attached to the direct-drive guide 228. The second moving member 230 has a pair of plates 230a disposed with a predetermined interval so as to face each other, and the first moving member 229 is disposed between the pair of plates 230a of the second moving member 230. The second moving member 230 moves so as to follow the movement of the first moving member 229 when the first moving member 229 moves by the driving of the drive belt 225.

Figure 9:
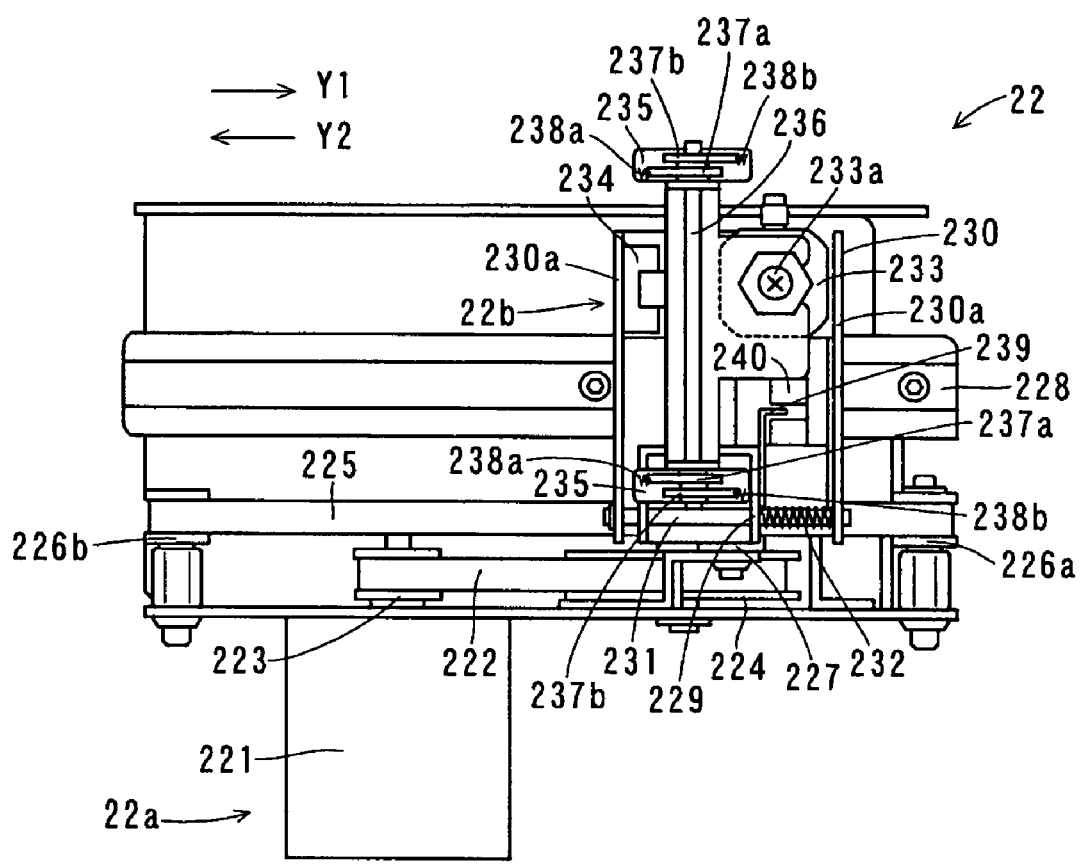
FIG. 9 is a plan view showing a state where conveyance of a rack by the first rack moving mechanism illustrated in FIG. 7 stops.

Concretely, a shaft 231 is attached between the pair of plates 230a of the second moving member 230, and the first moving member 229 is fit to the shaft 231 so as to slide in the extending directions (Y1 and Y2 directions) of the shaft 231. A compression spring 232 for energizing the first moving member 229 in the Y2 direction is attached to the shaft 231. Consequently, in the case where the first moving member 229 is moved in the Y1 direction by the drive belt 225 as shown in FIGS. 7 and 9 (in the case where the first moving member 229 is moved from the position in FIG. 7 to the position in FIG. 9), the first moving member 229 presses one of the plates 230a in the second moving member 230 in the Y1 direction via the compression spring 232, so that the second moving member 230 is moved in the Y1 direction along the direct-drive guide 228. In the case where the first moving member 229 is moved in the Y2 direction by the drive belt 225 (in the case where the first moving member 229 is moved from the position in FIG. 9 to the position in FIG. 7), the first moving member 229 moves the other plate 230a of the second moving member 230 in the Y2 direction, so that the second moving member 230 is moved in the Y2 direction along the direct-drive guide 228.

As shown in FIGS. 7 and 8, to the second moving member 230 of the rack conveying unit 22b, a cylinder 233 and a direct-drive guide 234 are attached. The cylinder 233 is disposed so that a cylinder rod 233a extends in a direction (Z direction) perpendicular to the mounting surface 21f of the storage plate 21, and the direct-drive guide 234 is disposed so as to extend in the Z direction. A shaft holder 235 is attached to the cylinder rod 233a and the direct-drive guide 234. When the cylinder rod 233a extends in the Z direction, the shaft holder 235 is moved in the extending direction (Z direction) of the direct-drive guide 234.

Figure 10:
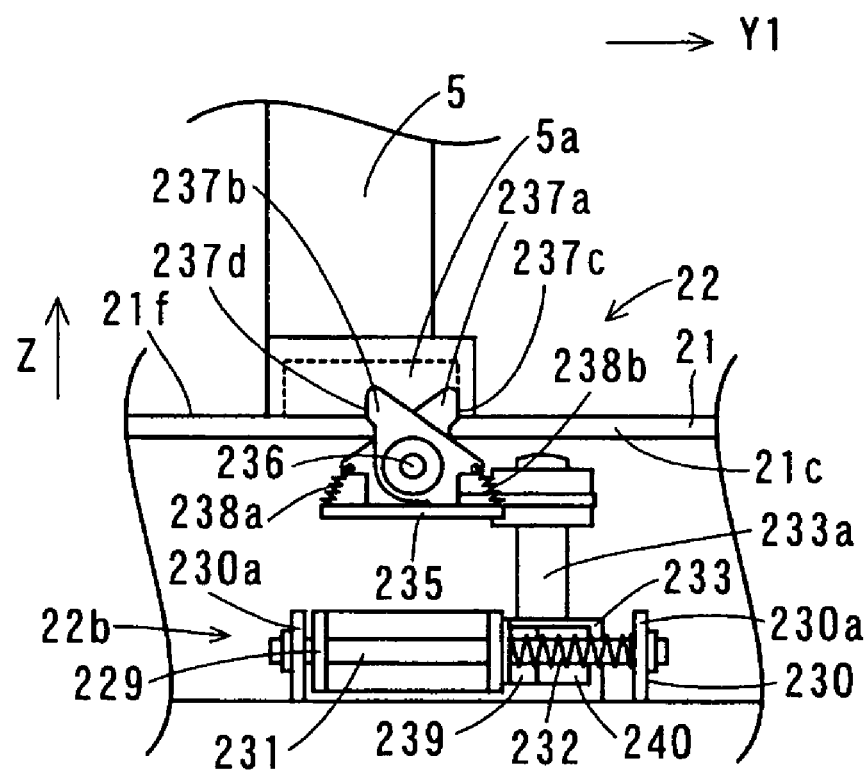
FIGS. 10 and 11 are side views showing a state where fitting nails of the first rack moving mechanism illustrated in FIG. 8 fit in the rack.
Figure 11:
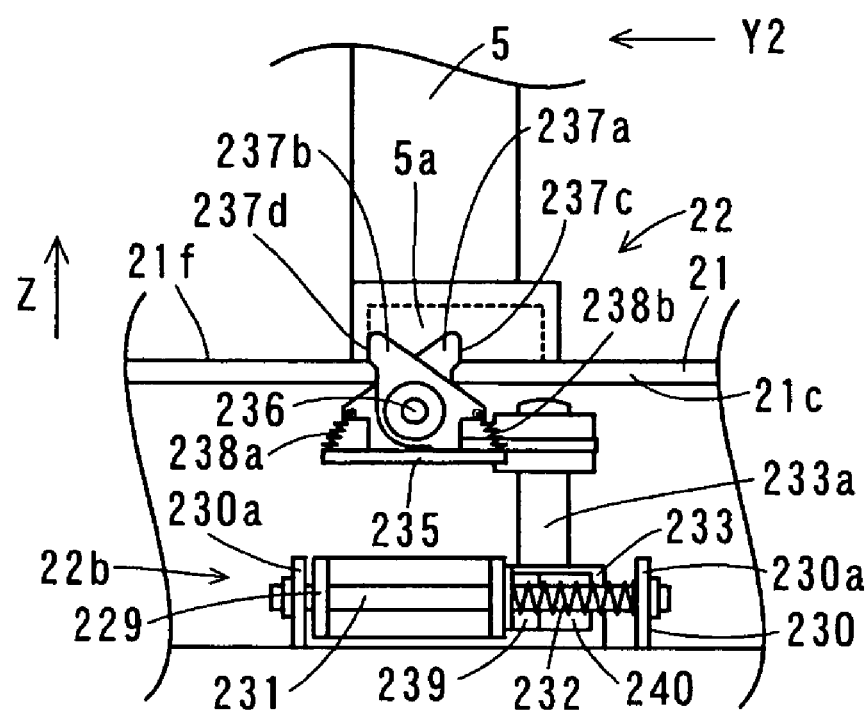

A shaft 236 is attached to the shaft holder 235 of the rack conveying unit 22b, and a pair of fitting nails 237a and a pair of fitting nails 237b are swingably attached to the shaft 236 around the axis of the shaft 236 as a fulcrum. One of the pair of fitting nails 237a is disposed at one end of the shaft 236, and the other fitting nail 237a is disposed at the other end of the shaft 236. One of the pair of fitting nails 237b is disposed at one end of the shaft 236, and the other fitting nail 237b is disposed at the other end of the shaft 236. Further, as shown in FIGS. 10 and 11, the fitting nails 237a and 237b are disposed so as to project from the mounting surface 21f via the pair of holes 21c in the storage plate 21 when the shaft holder 235 moves in the Z direction. The fitting nails 237a and 237b have fitting faces 237c and 237d which fit to the inner surface of the bottom 5a of the rack 5. Consequently, in the case of making the fitting nails 237a and 237b project from the mounting surface 21f and moving the rack conveying unit 22b in the Y1 direction (Y2 direction), the inner surface of the bottom 5a of the rack 5 engages with the fitting face 237c (237d) of the fitting nail 237a (237b), thereby moving the rack 5 in the Y1 direction (Y2 direction). In the case of moving the rack 5 in the Y1 direction, as shown in FIG. 10, the fitting nail 237a engages with the inner surface of the bottom 5a of the rack 5. In the case of moving the rack 5 in the Y2 direction, as shown in FIG. 11, the fitting nail 237b engages with the inner surface of the bottom 5a of the rack 5.

As shown in FIGS. 10 and 11, the fitting nail 237a of the rack conveying unit 22b is energized by a tension spring 238a attached to the shaft holder 235 so that the fitting face 237c and the inner surface of the bottom 5a of the rack 5 become parallel to each other. The fitting nail 237b is energized by a tension spring 238b attached to the shaft holder 235 so that the fitting face 237d and the inner surface of the bottom 5a of the rack 5 become parallel to each other. Consequently, when an external force is applied from above to the fitting nail 237a (237b), the fitting nail 237a (237b) is turned in a predetermined direction against the energization force of the tension spring 238a (238b). In the case where the external force from above to the fitting nail 237a (237c) is eliminated, the fitting nail 237a (237b) is turned in the direction opposite to the predetermined direction by the energization force of the tension spring 238a (238b) so that the fitting face 237c (237d) and the inner surface of the bottom 5a of the rack 5 become parallel to each other.

As shown in FIGS. 7 and 8, a detection piece 239 is attached to the first moving member 229 of the rack conveying unit 22b, and a transmission sensor 240 is attached to the second moving member 230. The detection piece 239 and the transmission sensor 240 are provided to detect that conveyance in the Y1 direction of the rack 5 by the first rack moving mechanism 22 is stopped. Concretely, the detection piece 239 and the transmission sensor 240 are disposed so that a state where light is shielded by the detection piece 239 is detected by the transmission sensor 240 in the case where the first moving member 229 moves in the Y1 direction when the second moving member 230 stops as shown in FIG. 9.

As shown in FIGS. 4 and 5, the transmission sensor 23 of the storing section 20 is provided to detect the presence/absence of the rack 5 in the storage area other than the transverse feed position P3. The transmission sensor 23 is disposed so as to detect a light shield state in the case where at least one rack 5 is stored in the storage area other than the transverse feed start position P3. The transmission sensor 24 is provided to detect that the rack 5 moved in the Y1 direction from the rack receive position P2 side reaches the transverse feed position P3. The transmission sensor 24 is disposed to detect a light shield state when the rack 5 arrives at the transverse feed start position P3.

Figure 12:
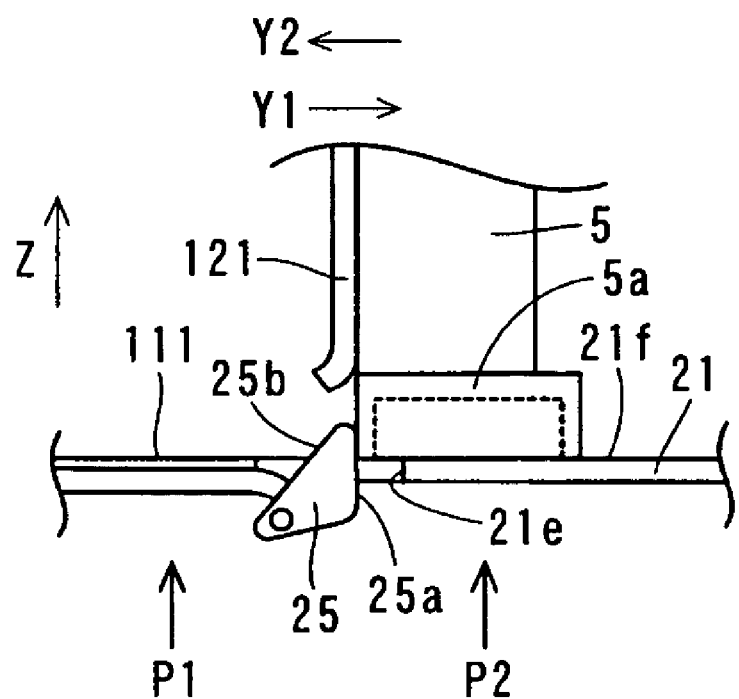
FIG. 12 is a side view showing the structure of the periphery of a reversal preventing member in the conveying device according to the first embodiment illustrated in FIGS. 4 and 5.
Figure 13:
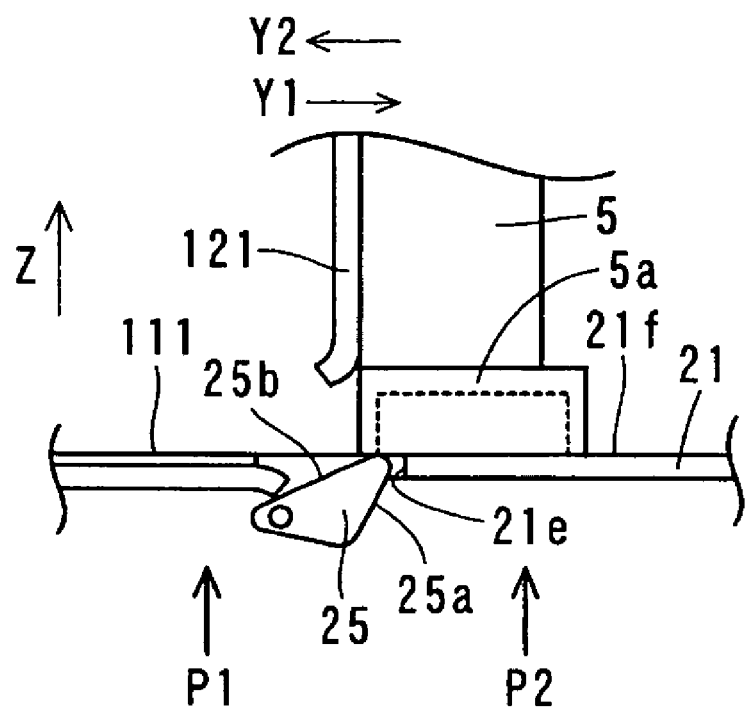
FIG. 13 is a side view showing a state where the reversal preventing member illustrated in FIG. 12 swings.

The reversal preventing members 25 in the storing section 20 are provided to prevent the rack 5 pushed from the push position P1 to the rack receive position P2 from moving back from the rack receive position P2 to the push position P1. The reversal preventing members 25 are disposed in areas corresponding to the notches 21e in the storage plate 21. The reversal preventing member 25 has, as shown in FIG. 12, a perpendicular surface 25a perpendicular to the mounting surface 21f of the storage plate 21 and a tilted surface 25b tilted from the perpendicular surface 25a by a predetermined angle. As shown in FIGS. 12 and 13, the reversal preventing member 25 swings below the storage plate 21 when the rack 5 passes the boundary between the push position P1 and the rack receive position P2 and, after the rack 5 passes the boundary between the push position P1 and the rack receive position P2, swings upward of the storage plate 21 to return in an initial state (state of FIG. 12). The reversal preventing member 25 is constructed so as not to swing in response to the external force in the Y2 direction.

Figure 14:
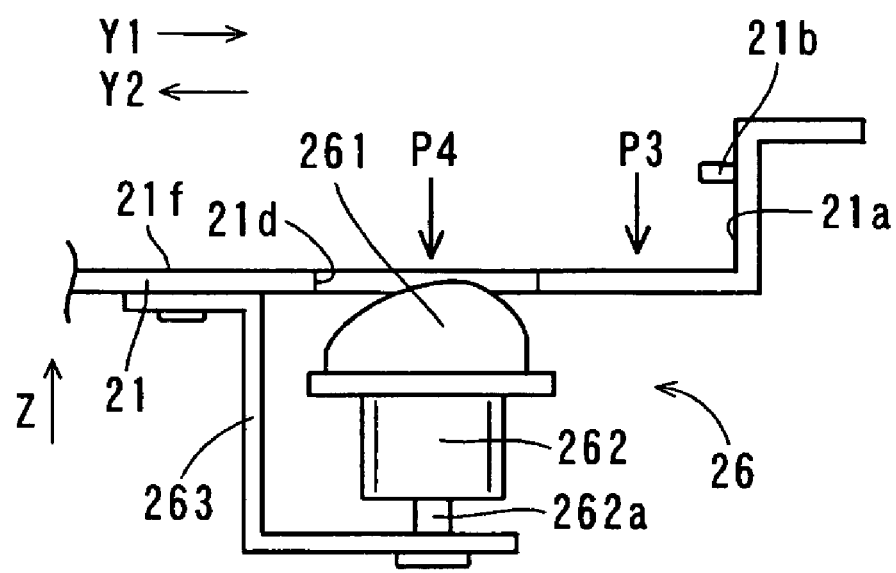
FIG. 14 is a side view showing the structure of the periphery of the storage regulating mechanism in the conveying device according to the first embodiment illustrated in FIGS. 4 and 5.
Figure 15:
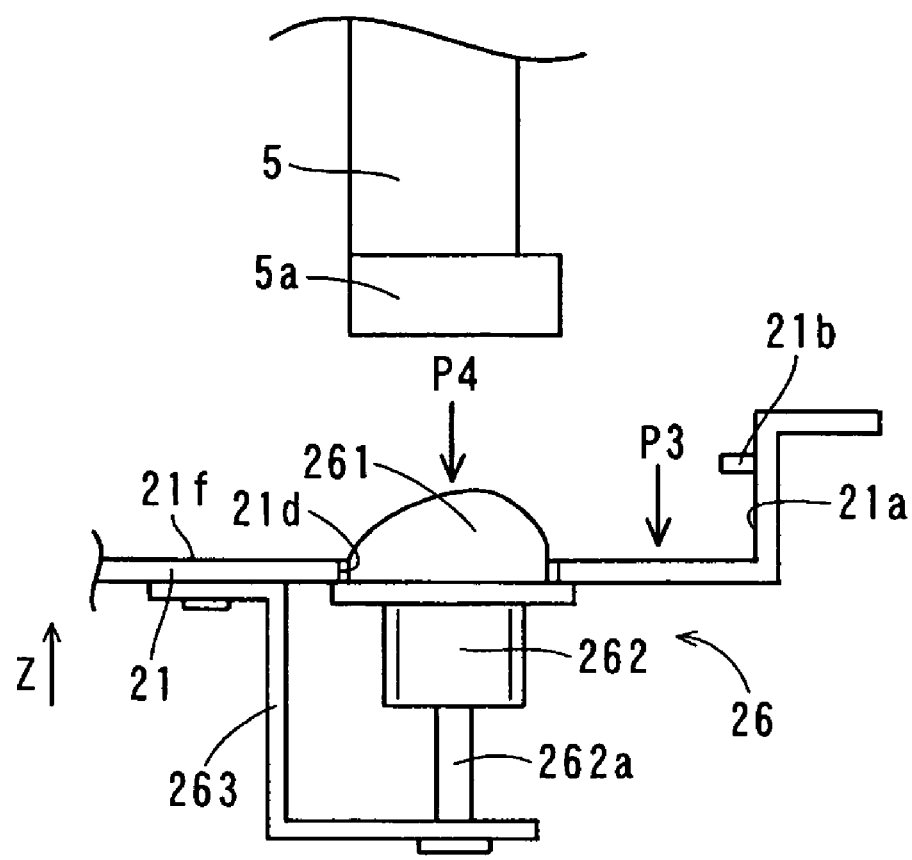
FIG. 15 is a side view showing a state where a preventing member of the storage regulating mechanism illustrated in FIG. 14 projects from a mounting surface of a storage plate.

In the first embodiment, as shown in FIGS. 4 and 5, the storage regulating mechanism 26 in the storing section 20 is provided to regulate storage of the rack 5 in the reserve storage position P4 in the storage plate 21. The storage regulating mechanism 26 has, as shown in FIGS. 5 and 14, a pair of preventing members 261 and a pair of cylinders 262. The cylinder 262 is disposed so that a cylinder rod 262a extends in a direction (Z direction) perpendicular to the mounting surface 21f of the storage plate 21. The cylinder rod 262a is attached to a surface opposite to the mounting surface 21f of the storage plate 21 via a bracket 263. Consequently, as shown in FIG. 15, when the cylinder rod 262a is extended in the Z direction, the body of the cylinder 262 moves in the Z direction toward the storage plate 21.

In the first embodiment, the preventing member 261 is attached to the body on the side opposite to the cylinder rod 262a of the cylinder 262. The preventing member 261 is disposed so as to project from the mounting surface 21f via the hole 21d in the storage plate 21 when the body of the cylinder 262 moves in the Z direction. As shown in FIG. 5, the preventing member 261 is formed in a rectangular shape in plan view like the hole 21d in the storage plate 21 and has a length in the longer direction substantially the same as the length in the shorter direction of the rack 5 (bottom 5a). Consequently, as shown in FIG. 15, when the preventing member 261 projects from the mounting surface 21f, storage of the rack 5 into the reserve storage position P4 is prevented by the preventing member 261. When the preventing member 261 projects from the mounting surface 21f, the distance between an end on the transverse feed start position P3 side of the preventing member 261 and an end on the transverse feed start position P3 side of the storage regulating part 21b of the storage plate 21 is smaller than the length in the shorter direction of the rack 5 (bottom 5a), so that storage of the rack into the transverse start position P3 is also prevented.

As shown in FIGS. 4 and 5, the barcode reader 27 in the storing section 20 is provided to read a barcode on the rack 5 moving from the rack receive position P2 side to the transverse feed start position P3.

The conveying section 30 of the conveying device 1 is provided to convey the rack 5 carried to the transverse feed start position P3 to the sample supplying position 2a (3a) and the carrying-out section 40. Further, in the first embodiment, the conveying section 30 also has the function of moving the rack 5 conveyed to the carrying-out section 40 side again to the transverse feed start position P3 in the direction opposite to the conveyance direction in the case where a re-analysis is conducted. The conveying section 30 includes, as shown in FIGS. 16 and 17, a transverse feed plate 31, a driver 32, a rack conveyer 33, and a detector 34.

In a conveyance surface 31a of the transverse feed plate 31 in the conveying section 30, a hole 31b extending from the transverse feed start position P3 to an ejection start position P5 which will be described later is formed as shown in FIG. 5.

Figure 16:
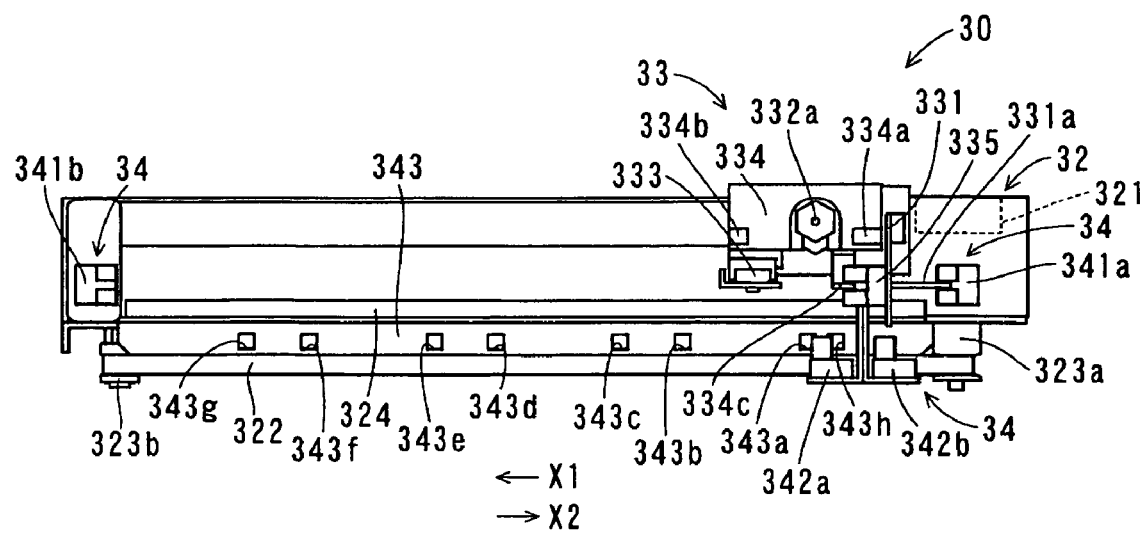
FIG. 16 is a plan view showing the structure of a conveying section in the conveying device according to the first embodiment illustrated in FIGS. 4 and 5.
Figure 17:
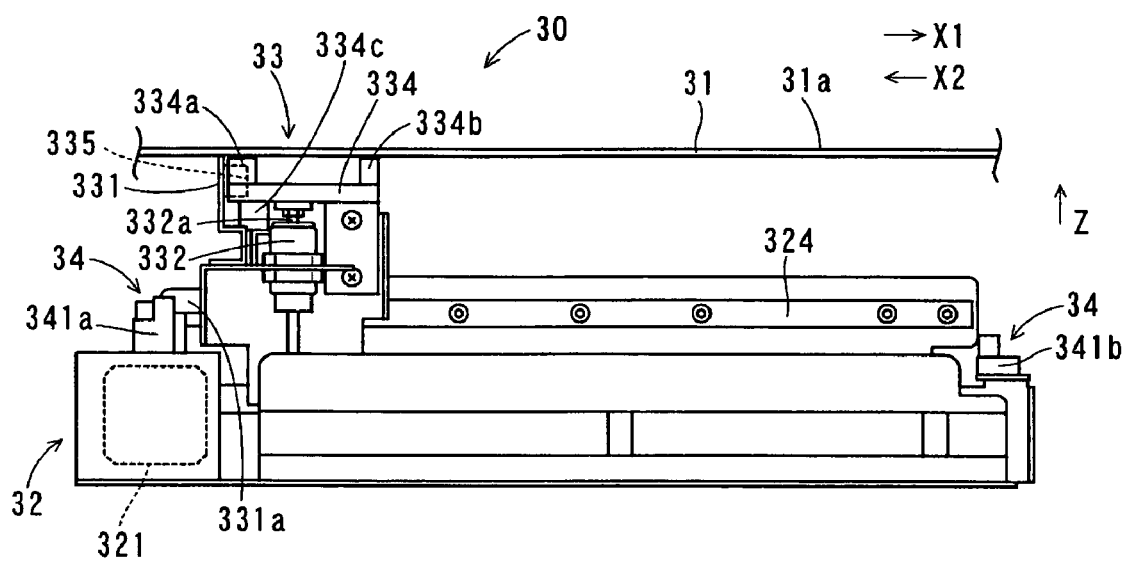
FIG. 17 is a side view of the conveying section shown in FIG. 16.

As shown in FIGS. 16 and 17, the driver 32 in the conveying section 30 is provided to move the rack conveyer 33 in an X1 direction (conveyance direction) and an X2 direction (direction opposite to the conveyance direction), and is disposed below the conveyance surface 31a of the transverse feed plate 31. The driver 32 is constructed by a motor 321, a drive belt 322, pulleys 323a and 323b, and a direct-drive guide 324. The motor 321 is coupled to the pulley 323a, and the drive belt 322 is attached to the pulleys 323a and 323b. Consequently, when the motor 321 is driven, the drive belt 322 is driven via the pulley 323a. The direct-drive guide 324 is disposed so as to extend in the X1 direction (X2 direction).

In the first embodiment, as shown in FIGS. 4 and 5, the rack conveyer 33 in the conveying section 30 has, in addition to the function of moving the rack 5 on the conveyance surface 31a of the transverse feed plate 31 from the transverse feed start position P3 to the ejection start position P5 side (X1 direction), the function of moving the rack 5 from the ejection start position P5 side to the transverse feed start position P3 (X2 direction). In the conveying section 30, an initial position 30a in FIG. 5 is a position from which transverse feed of the rack 5 by the rack conveyer 33 starts. A transverse feed end position 30b in FIG. 5 is a position in which the transverse feed of the rack 5 by the rack conveyer 33 is finished. The rack conveyer 33 includes, as shown in FIGS. 16 and 17, a moving member 331, a solenoid 332, a direct-drive guide 333, a fitting member 334, and a transmission sensor 335. The moving member 331 is coupled to the drive belt 322 and is also attached to the direct-drive guide 324. Consequently, when the drive belt 322 is driven, the moving member 331 moves in the extending directions (X1 and X2 directions) of the direct-drive guide 324. The solenoid 332 is attached to the moving member 331, and a rod 322a of the solenoid 332 extends in a direction (Z direction) perpendicular to the conveyance surface 31a of the transverse feed plate 31. The direct-drive guide 333 is attached to the moving member 331 and is disposed so as to extend in the Z direction. The fitting member 334 is attached to the rod 322a of the solenoid 332 and the direct-drive guide 333. With the configuration, when the rod 332a of the solenoid 332 extends in the Z direction, the fitting member 334 is moved in the direction (Z direction) in which the direct-drive guide 333 extends.

Figure 18:
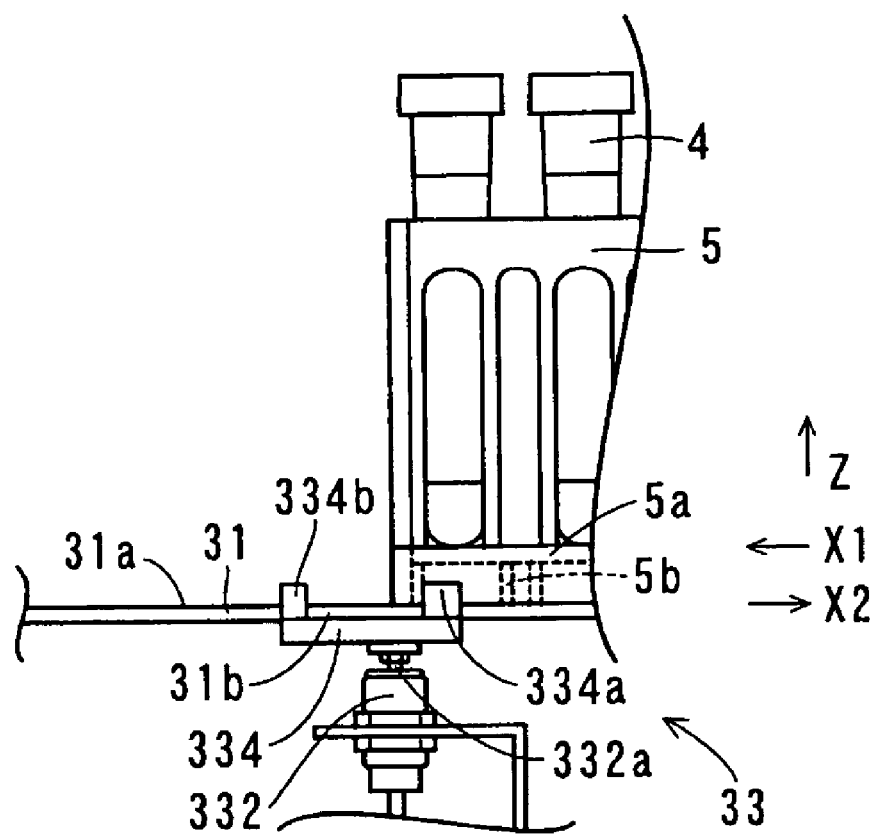
FIGS. 18 and 19 are side views showing a state where a fitting member of the conveying section illustrated in FIG. 17 fits in a rack.
Figure 19:
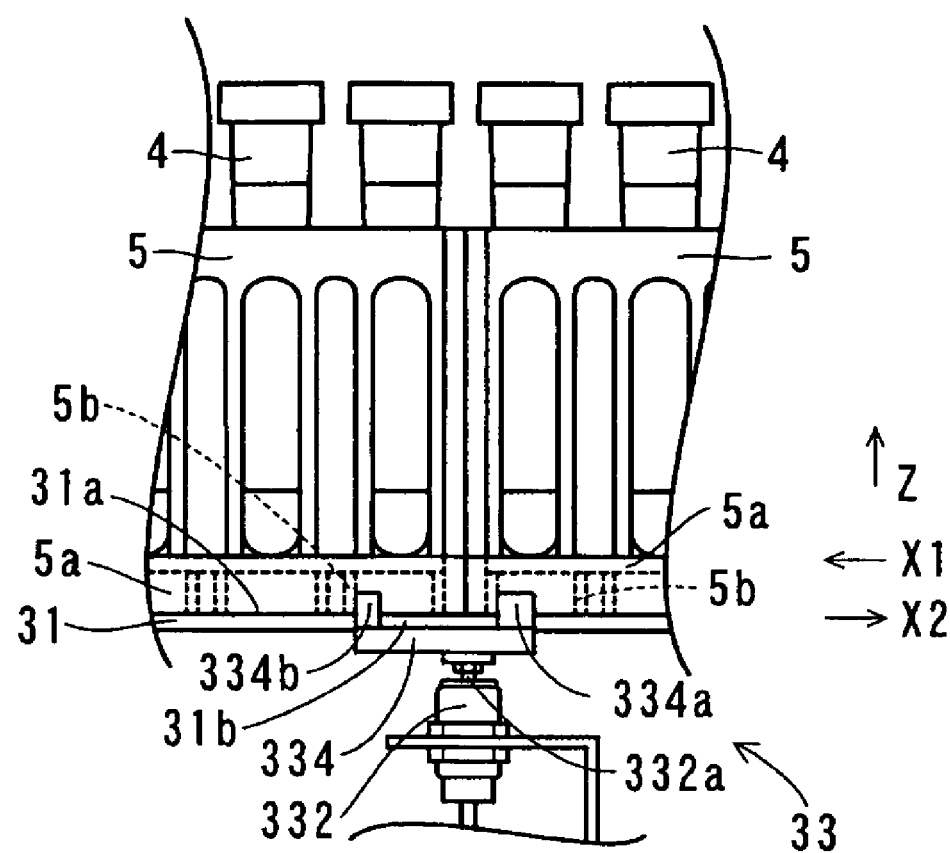

A first fitting part 334a and a second fitting part 334b are integrally provided for the fitting member 334 of the rack conveyer 33. The first and second fitting parts 334a and 334b are provided so as to project from the conveyance surface 31a via the holes 31b in the transverse feed plate 31 when the fitting member 334 moves in the Z direction as shown in FIGS. 18 and 19. As shown in FIG. 18, when the first and second fitting parts 334a and 334b are projected from the conveyance surface 31a and the rack conveyer 33 is moved in the X1 direction, the inner surface on the first sample container 4 side of the rack 5 fits to the first fitting part 334a, thereby moving the rack 5 in the X1 direction. Further, as shown in FIG. 19, the plate 5b on the 10th sample container 4 side of the rack 5 is fit to the second fitting part 334b and the inner surface of the first sample container 4 side of the rack 5 is fit to the first fitting part 334a, thereby moving two racks 5 serially, simultaneously in the X1 direction. FIGS. 18 and 19 show a state where the racks 5 are moved in the X1 direction. Specifically, in FIG. 18, in the case of moving the rack 5 in the X2 direction, the first fitting part 334a fits to the plate 5b on the first sample container 4 side of the rack 5. In FIG. 19, in the case of moving the rack 5 in the X2 direction, the first fitting part 334a fits to the plate 5b on the first sample container 4 side of the rack 5, and the second fitting part 334b fits to the inner surface on the 10th sample container 4 side of the rack 5.

As shown in FIGS. 16 and 17, the transmission sensor 335 in the rack conveyer 33 is provided to detect projection of the first and second fitting parts 334a and 334b from the conveyance surface 31a of the transverse feed plate 31. The transmission sensor 335 is disposed so that light is shielded by a detection piece 334c attached to the fitting member 334 in the case where the first and second fitting parts 334a and 334b project from the conveyance surface 31a of the transverse feed plate 31.

The detector 34 in the conveying section 30 is provided to detect the position of the rack conveyer 33 that moves in the X1 and X2 directions. The detector 34 is constructed by transmission sensors 341a and 341b, transmission sensors 342a and 342b, and a detection plate 343. The transmission sensor 341a is provided to detect that the rack conveyer 33 has moved to the initial position 30a (refer to FIG. 5). The transmission sensor 341a is disposed so as to detect that light is shielded by the detection piece 331a of the moving member 331 as a component of the rack conveyer 33 when the rack conveyer 33 is moved to the initial position 30a. The transmission sensor 341b is provided to detect that the rack conveyer 33 has moved to the transverse feed end position 30b (refer to FIG. 5). The transmission sensor 341b is disposed so as to detect that light is shielded by a detection piece (not shown) of the moving member 331 as a component of the rack conveyer 33 when the rack conveyer 33 is moved to the transverse feed end position 30b.

The transmission sensors 342a and 342b of the detector 34 are attached to the moving member 331 as a component of the rack conveyer 33. The transmission sensors 342a and 342b are disposed with a predetermined interval in the movement directions (X1 and X2 directions) of the rack conveyer 33. The detection plate 343 of the detector 34 has a plurality of rectangular detection holes 343a to 343h arranged along the movement directions (X1 and X2 directions) of the rack conveyer 33. The detection holes 343a to 343h are provided so change the transmission sensors 342a and 342b to a transmission (on) state or a light shield (off) state. In the case of moving the rack conveyer 33 in the X1 direction at a pitch of about 20 mm, the detection holes 343a to 343h are disposed so that the state (on/off state) of at least one of the transmission sensors 342a and 342b changes each time the rack conveyer 33 moves one pitch in the X1 direction. Therefore, each time the rack conveyer 33 is moved one pitch in the X1 direction, the combination of the on/off states in the transmission sensors 342a and 342b changes. That is, according to the combination of the on/off states in the transmission sensors 342a and 342b, the position of the rack conveyer 33 is detected.

In the case where the transmission sensor 342a is positioned in an area corresponding to the detection hole 343a in the detector 34, the rack conveyer 33 is in the initial position 30a (refer to FIG. 5). When the transmission sensor 342a is positioned in an area corresponding to the detection hole 343g, the rack conveyer 33 is in the transverse feed end position 30b (refer to FIG. 5). The detection holes 343a to 343g are disposed in order in the X1 direction (from the initial position 30a to the transverse feed end position 30b). The detection hole 343h is disposed with a predetermined interval in the X2 direction of the detection hole 343a.

As shown in FIGS. 4 and 5, the carrying-out section 40 in the conveying device 1 is provided to carry the rack 5 conveyed from the conveying section 30 to the carrying-out section 40 to a position in which the rack 5 can be ejected from an outlet 1b by the unloading section 50. The carrying-out section 40 includes an ejection plate 41, a second rack moving mechanism 42, and transmission sensors 43 and 44.

The ejection plate 41 in the carrying-out section 40 has a rack contact part 41a and a pair of holes 41b. The area of the size of one rack 5 on the conveying section 30 side in the ejection plate 41 is the ejection start position P5 from which conveyance of the rack 5 starts in the carrying-out section 40. The area of the size of one rack 5 on the side (unloading section 50 side) opposite to the ejection start position P5 in the ejection plate 41 is an unloading start position P6 from which unloading from the outlet 1b of the rack 5 by the unloading section 50 starts. The rack contact part 41a is provided on the ejection start position P6 side of the ejection plate 41. The rack contact part 41a is formed by folding the ejection plate 41 in the direction perpendicular to an ejection surface 41c. The pair of holes 41b in the ejection plate 41 is formed so as to extend from the ejection start position P5 to the unloading start position P6 in the ejection plate 41.

The second rack moving mechanism 42 in the carrying-out section 40 is provided to move the rack 5 on the ejection surface 41c of the ejection plate 41 in the Y2 direction and is disposed below the ejection surface 41c of the ejection plate 41. The second rack moving mechanism 42 has a pair of fitting members 421 which fit to the inner surface of the bottom 5a of the rack 5 when the rack 5 is moved in the Y2 direction. The fitting members 421 are disposed in areas corresponding to the holes 41b in the ejection plate 41 and are movable in the Y2 direction (Y1 direction) along the holes 41b by the driver in the not-shown second rack moving mechanism 42. Further, the fitting members 421 project from the ejection surface 41c via the holes 41b in the ejection plate 41 when the rack 5 is moved in the Y2 direction.

The transmission sensor 43 in the carrying-out section 40 is provided to detect arrival at the ejection start position P5 of the rack 5 moved in the X1 direction from the conveying section 30. The transmission sensor 43 is disposed so that light is shielded when the rack 5 arrives at the ejection start position P5. The transmission sensor 44 in the carrying-out section 40 is provided to detect arrival at the unloading start position P6 of the rack 5 moved in the Y2 direction from the ejection start position P5. The transmission sensor 44 is disposed so that light is shielded when the rack 5 arrives at the unloading start position P6.

The unloading section 50 of the conveying device 1 is provided to unload the rack 5 conveyed to the unloading start position P6 in the carrying-out section 40 from the outlet 1b. The unloading section 50 includes a rack conveying member 51, a motor 52, a drive belt 53, pulleys 54a and 54b, and a direct-drive guide 55.

The rack conveying member 51 in the unloading section 50 is provided to move the rack 5 conveyed to the unloading start position P6 in the X1 direction (outlet 1b side). The motor 52 is coupled to the pulley 54a and the drive belt 53 is attached to the pulleys 54a and 54b. When the motor 52 drives, the drive belt 53 is driven via the pulley 54a. The direct-drive guide 55 is disposed so as to extend in the X1 direction (X2 direction). The rack conveying member 51 is coupled to the drive belt 53 and is also attached to the direct-drive guide 55. By driving the drive belt 53, the rack conveying member 51 is moved in the extending directions (X1 and X2 directions) of the direct-drive guide 55.

In the first embodiment, as described above, by constructing the first rack moving mechanism 22 for conveying the rack 5 received in the rack receive position P2 to the transverse feed start position P3 in the storing section 20 so as to be able to move the rack 5 in the direction opposite to the conveyance direction from the transverse feed start position P3 side to the rack receive position P2 side, the rack 5 can be moved in the direction opposite to the conveyance direction from the transverse feed start position P3 side to the rack receive position P2 side by the first rack moving mechanism 22 without requiring an operator. Consequently, at the time of re-analyzing the sample in the sample container 4 held on the first rack 5 by the same analyzer (the first blood analyzer 2 or the second blood analyzer 3), the first rack 5 conveyed from the transverse feed start position P3 to the sample supplying position 2a (3a) can be conveyed in the reserve direction back to the transverse feed start position P3 and re-stored in the storing section 20. In the case of re-conveying the re-stored first rack 5 from the transverse feed start position P3 to the sample supplying position 2a (3a), the second rack 5 already conveyed to the transverse feed start position P3 by the first rack 5 moving mechanism 22 can be moved to an area other than the transverse feed start position P3 in the storing section 20 by the first rack moving mechanism 22 without requiring an operator. Thus, an area (transverse feed start position P3) for re-storing the first rack 5 can be assured in the storing section 20. As a result, at the time of re-analyzing the sample in the same analyzer (first blood analyzer 2 or the second blood analyzer 3), the rack 5 (sample) can be re-conveyed to the first blood analyzer 2 or the second blood analyzer 3 without requiring an operator.

In the first embodiment, the first rack moving mechanism 22 is constructed so as to include the fitting nails 237a and 237b which fit to the rack 5, so that the racks 5 can be moved one by one with the fitting nails 237a and 237b of the first rack moving mechanism 22. In this case, by setting the area of the size of one rack 5 adjacent to the rack receive position P2 side of the transverse feed start position P3 as the area (reserve storage position P4) in which storage of the rack 5 is prevented, at the time of re-analyzing the sample in the sample container 4 held on the first rack 5 by the same analyzer (the first blood analyzer 2 or the second blood analyzer 3), by conveying only the second rack 5 already carried to the transverse feed start position P3 to the area (reserve storage position P4) adjacent to the rack receive position P2 side of the transverse feed start position P3, an area (transverse feed start position P3) for re-storing the first rack 5 can be easily assured in the storing section 20.

In the first embodiment, by providing the preventing members 261 for regulating storage of the rack 5 in the area (reserve storage position P4) in which storage of the rack 5 is regulated, storage of the rack 5 into the area (reserve storage position P4) in which storage of the rack 5 is regulated can be easily prevented by the preventing members 261.

In the first embodiment, by disposing the preventing members 261 below the mounting surface 21f of the storing section 20 and allowing the preventing members 261 project from the mounting surface 21f, in the case where the rack 5 is moved from the transverse feed start position P3 side to the rack receive position P2 side (in the case of re-analyzing the sample) and in the case where the rack 5 does not exist in the transverse feed start position P3 and is moved from the rack receive position P2 side to the transverse feed start position P3 side (in the case of conveying the rack 5 to the transverse feed start position P3 at the time of normal conveyance), by housing the preventing members 261 below the mounting surface 21f of the storing section 20, movement from the transverse feed start position P3 side to the rack receive position P2 side or from the rack receive position P2 side to the transverse feed start position P3 side is not disturbed by the preventing members 261. By allowing the preventing members 261 project from the mounting surface 21f of the storing section 20 in the case where the rack 5 exists in the transverse feed start position P3 and the rack 5 is moved from the rack receive position P2 side to the transverse feed start position P3 side, storage of the rack 5 into the area (reserve storage position P4) in which storage of the rack 5 is regulated can be prevented by the preventing members 261.

In the first embodiment, the conveying section 30 for conveying the rack 5 conveyed to the transverse feed start position P3 to the sample supplying position 2a (3a) and the ejection start position P5 is constructed so as to be able to move the rack 5 in the direction opposite to the conveyance direction from the ejection start position P5 side to the transverse feed start position P3. With the configuration, at the time of re-analyzing the sample in the sample container 4 held on a predetermined rack 5 by the same analyzer (the first blood analyzer 2 or the second blood analyzer 3), the predetermined rack 5 conveyed from the transverse feed start position P3 to the sample supplying position 2a (3a) by the conveying section 30 can be easily conveyed again to the transverse feed start position P3.

FIGS. 20 to 39 are schematic diagrams illustrating the conveying operation of the conveying device according to the first embodiment of the invention. With reference to FIGS. 1, 5, and 9 and FIGS. 20 to 39, the conveying operation of the conveying device 1 according to the first embodiment will be described.

Figure 20:
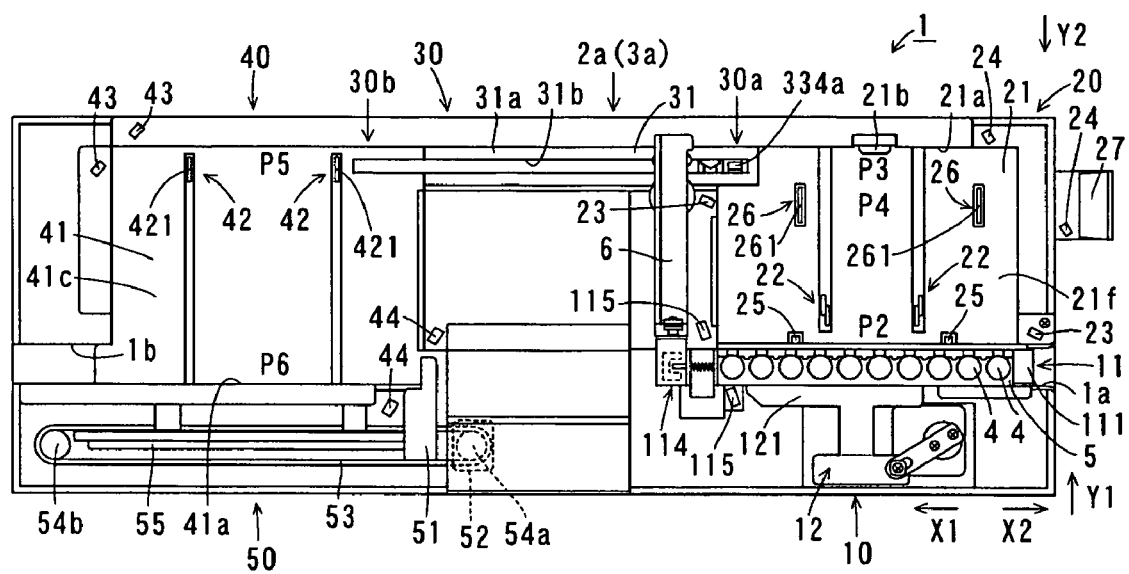
FIGS. 20 to 29 are schematic diagrams illustrating conveying operation of the conveying device according to the first embodiment shown in FIGS. 4 and 5.

First, as shown in FIG. 20, the first rack 5 is introduced into the rack receiver 10 in the conveying device 1 via the inlet 1a. At this time, the conveyance belt 111 in the rack loading mechanism 11 is driven in the rack receiver 10. Consequently, the first rack 5 is conveyed from the inlet 1a to the push position P1 (refer to FIG. 5) by the conveyance belt 111. The detector 114 detects that the first rack 5 arrives at the push position P1. The transmission sensor 115 detects the existence of the first rack 5 in the push position P1.

Figure 21:
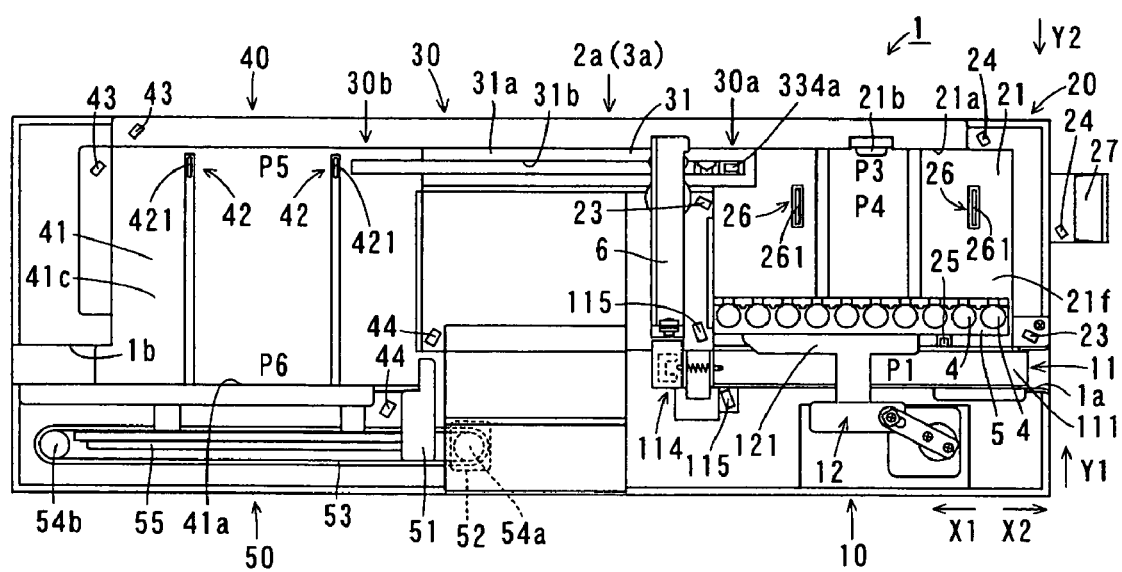

As shown in FIG. 21, in the rack receiver 10, after the first rack 5 is conveyed to the push position P1, the pushing member 121 of the rack pushing mechanism 12 is moved in the Y1 direction. By the operation, the first rack 5 is pushed from the push position P1 to the rack receive position P2 (refer to FIG. 5). At this time, the transmission sensor 115 detects that the first rack 5 is pushed from the push position P1 to the rack receive position P2. The transmission sensor 23 in the storing section 20 detects the existence of the first rack 5 in the rack receive position P2 (storage area other than the transverse feed start position P3 in the storing section 20).

Figure 22:
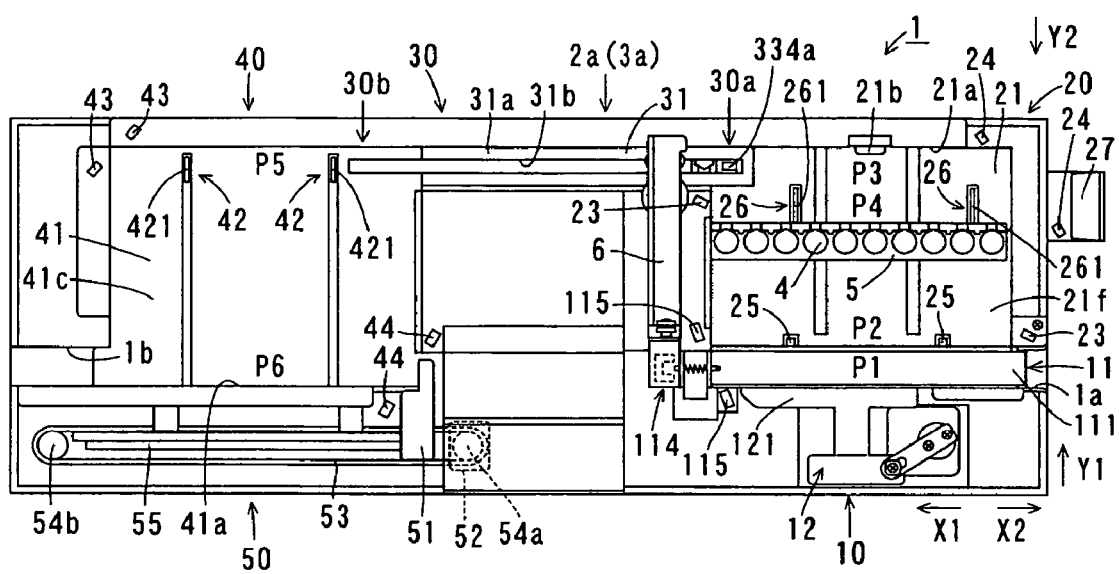

After that, as shown in FIG. 22, the first rack 5 pushed to the rack receive position P2 is moved in the Y1 direction by the fitting nails 237a (refer to FIG. 5) of the first rack moving mechanism 22 in the storing section 20. At this time, the preventing members 261 in the storage regulating mechanism 26 are housed below the mounting surface 21f of the storage plate 21.

Figure 23:
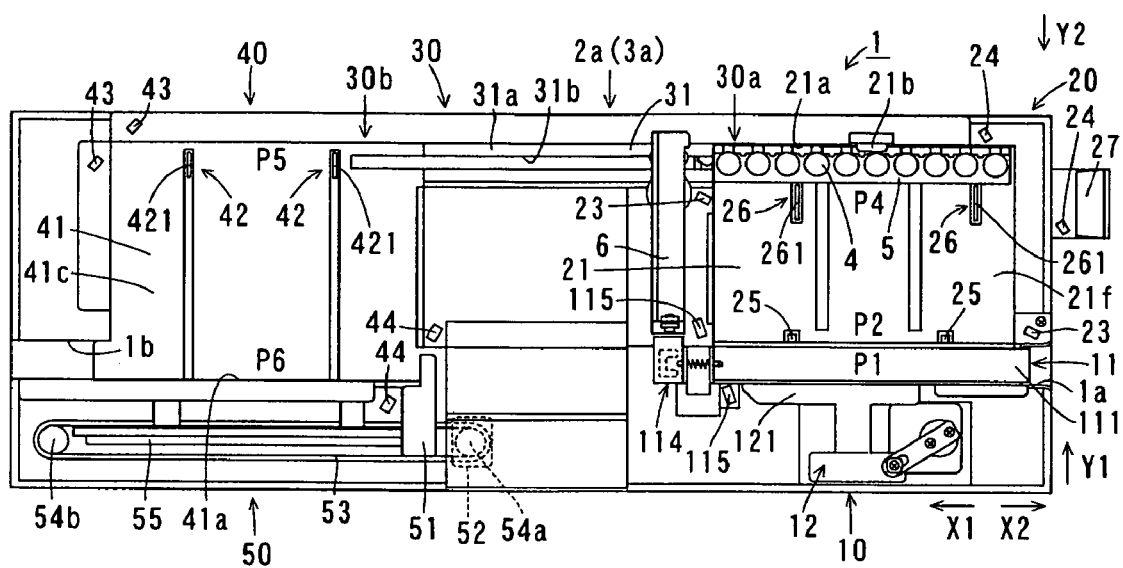

Consequently, as shown in FIG. 23, the first rack 5 moved in the Y1 direction by the fitting nails 237a (refer to FIG. 5) of the first rack moving mechanism 22 is conveyed to the transverse feed start position P3 (refer to FIG. 5) without disturbance of movement in the Y1 direction by the preventing members 261. Arrival of the first rack 5 at the transverse feed start position P3 is detected by the transmission sensor 24.

When the first rack 5 arrives at the transverse feed start position P3 (refer to FIG. 5) in the storing section 20, the first rack 5 comes into contact with the rack contact part 21a of the storage plate 21, thereby stopping the movement in the Y1 direction of the first rack 5. At this time, as shown in FIG. 9, the rack conveying unit 22b as a component of the first rack moving mechanism 22 operates as follows. To the first moving member 229 of the rack conveying unit 22b, the drive belt 225 driven by the motor 221 is coupled but the fitting nail 237a which fits to the first rack 5 is not attached. In a state where the motor 221 drives, movement in the Y1 direction of the first moving member 229 continues. On the other hand, to the second moving member 230 of the rack conveying unit 22b, the drive belt 225 is not coupled and the fitting nails 237a which fits the first rack 5 are attached via various parts, so that movement in the Y1 direction of the second moving member 230 is stopped. Therefore, only the first moving member 229 moves in the Y1 direction against the energizing force of the compression spring 232, so that the transmission sensor 240 attached to the second moving member 230 enters a light shield state by the detection piece 239 attached to the first moving member 229. As a result, completion of conveyance of the first rack 5 to the transverse feed start position P3 by the first rack moving mechanism 22 is detected.

Figure 24:
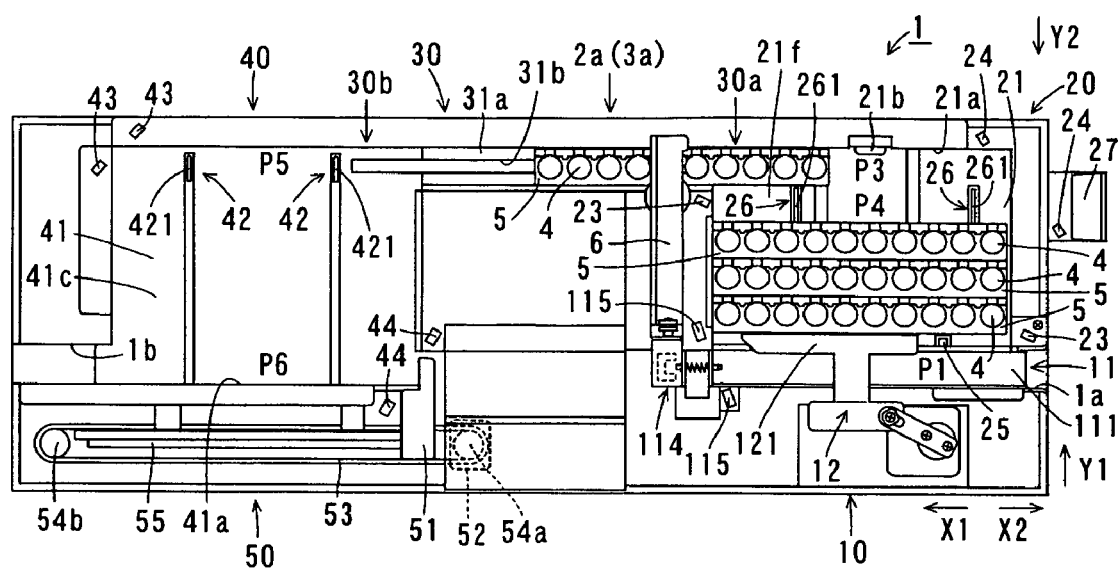

After that, as shown in FIG. 24, by moving the first rack 5 conveyed to the transverse feed start position P3 at a pitch of about 20 mm (pitch between neighboring sample containers 4) by the conveying section 30, the sample containers 4 held on the first rack 5 are sequentially conveyed to the sample supplying position 2a (3a). The second to fourth racks 5 are conveyed to the storage area in the storing section 20 in a manner similar to the first rack 5. At this time, in the storing section 20, the preventing members 261 of the storage regulating mechanism 26 are allowed to project from the mounting surface 21f of the storage plate 21. Consequently, conveyance of the second and subsequent racks 5 to the reserve storage position P4 is regulated by the preventing members 261.

Figure 25:
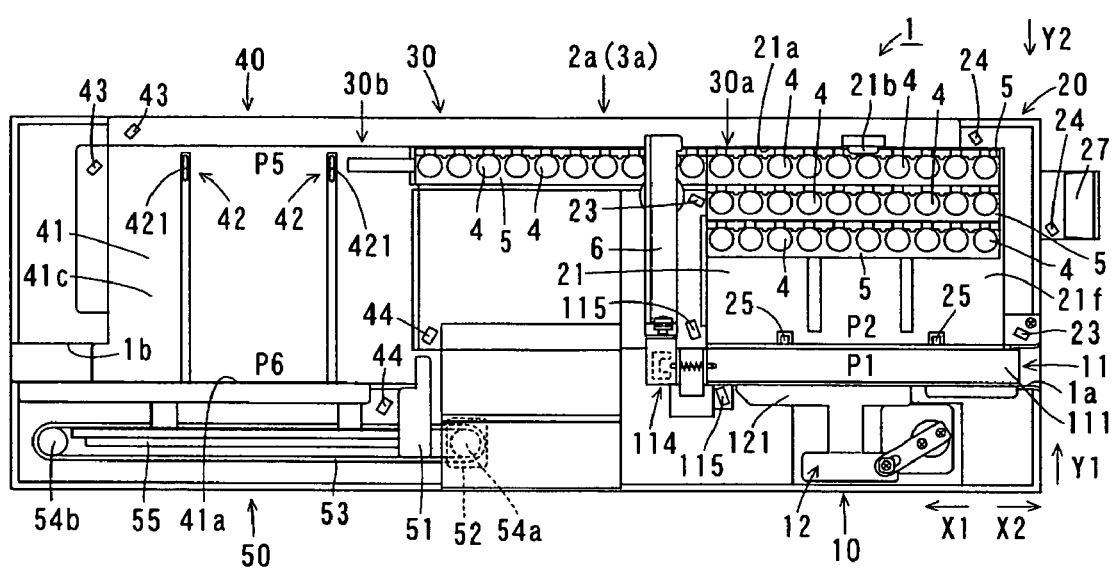

As shown in FIG. 25, when the first rack 5 is completely moved from the transverse feed start position P3 in the storing section 20, the preventing members 261 (refer to FIG. 5) of the storage regulating mechanism 26 are housed below the mounting surface 21f of the storage plate 21. In a state where the preventing members 261 are housed below the mounting surface 21f of the storage plate 21, the second to fourth racks 5 are moved in the Y1 direction by the fitting nails 237a (refer to FIG. 5) of the first rack moving mechanism 22. Until the second rack 5 is conveyed to the transverse feed start position P3 (refer to FIG. 5), the second to fourth racks 5 are moved in the Y1 direction.

Figure 26:
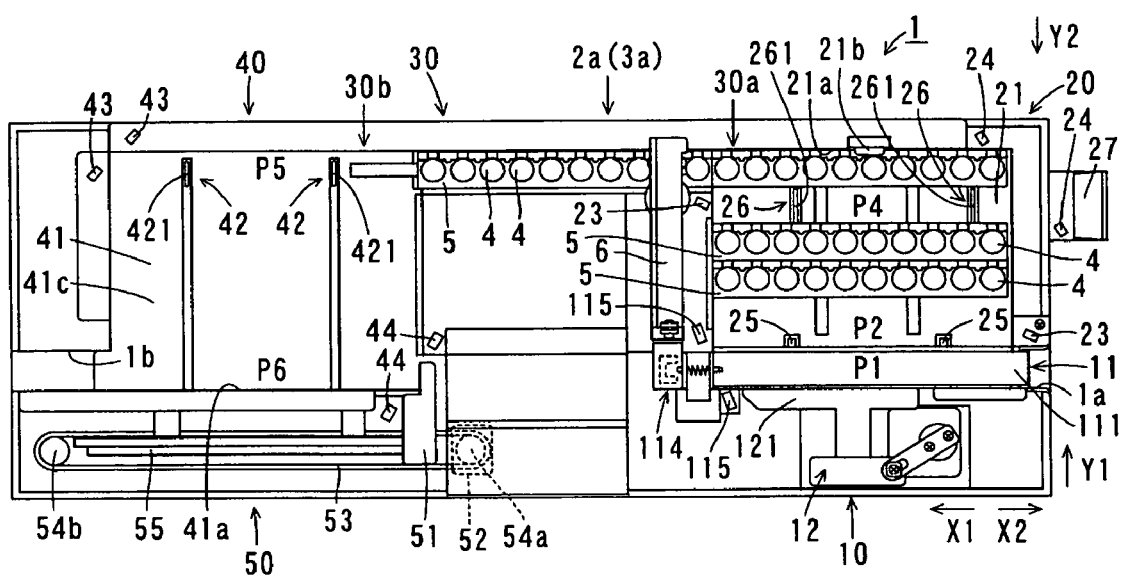

After that, as shown in FIG. 26, in the storing section 20, the third and fourth racks 5 are moved in the Y2 direction as a direction opposite to the conveyance direction by the fitting nails 237b (refer to FIG. 5) of the first rack moving mechanism 22. Until the third rack 5 is conveyed to the storage area adjacent to the reserve storage position P4, the third and fourth racks 5 are moved in the Y2 direction. After that, the preventing members 261 of the storage regulating mechanism 26 are allowed to project from the mounting surface 21f of the storage plate 21.

The operation performed in the case where it is determined that a re-analysis is necessary on the sample in the sample container 4 held on the first rack 5 in the state shown in FIG. 26 will be described.

Figure 27:
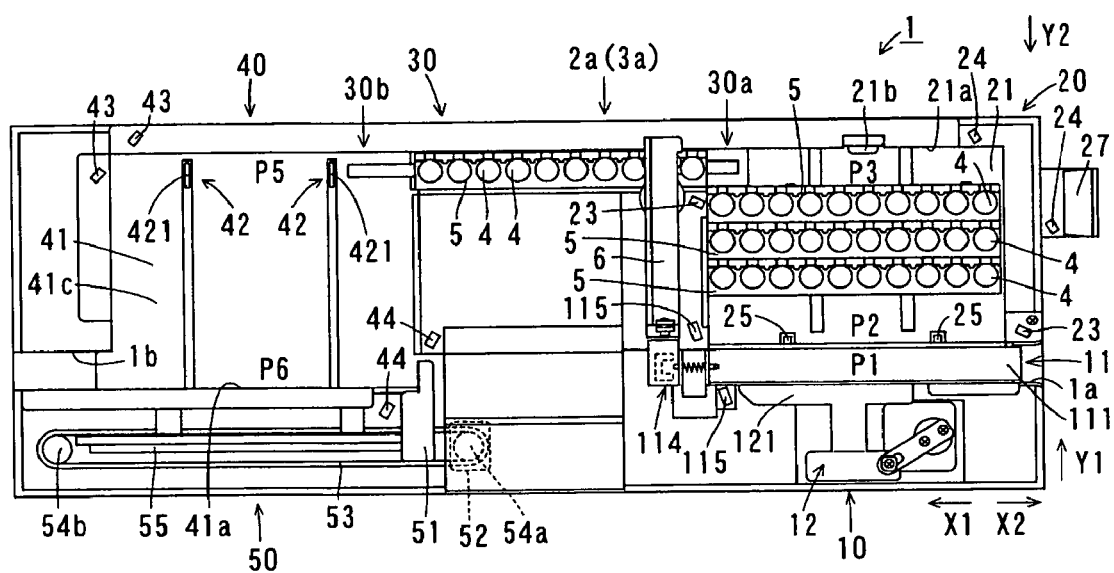

In the case where a re-analysis is determined on the sample in the sample container 4 held on the first rack 5, as shown in FIG. 27, first, in the storing section 20, the preventing members 261 (refer to FIG. 5) of the storage regulating mechanism 26 are housed below the mounting surface 21f of the storage plate 21. After that, in a state where the preventing members 261 are housed below the mounting surface 21f of the storage plate 21, the second rack 5 is conveyed to the reserve storage position P4 (refer to FIG. 5) by the fitting nails 237b (refer to FIG. 5) in the first rack moving mechanism 22.

Figure 28:
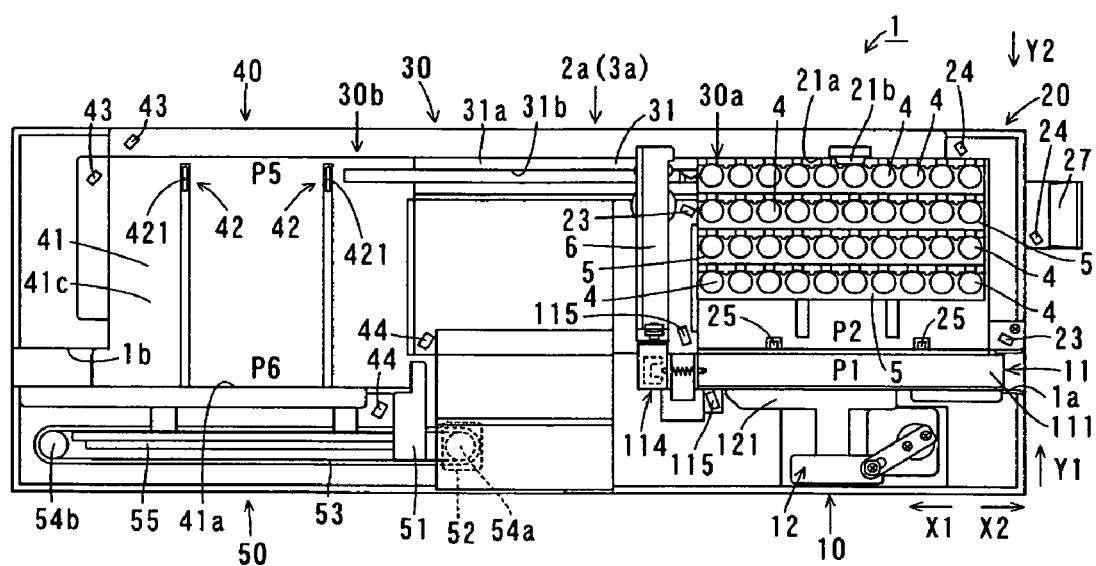
Figure 29:
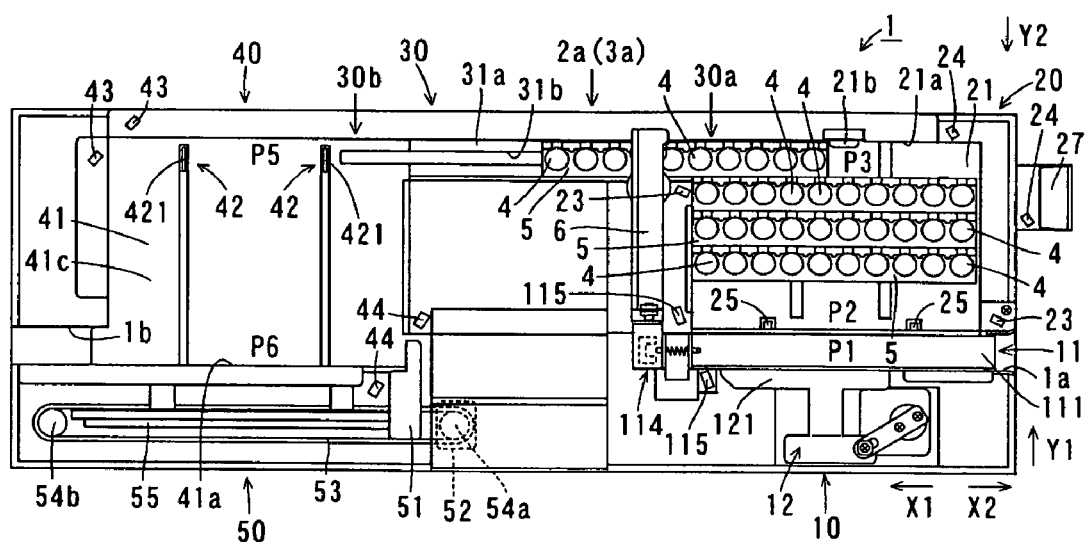

Nest, as shown in FIG. 28, by moving the first rack 5 in the X2 direction (the direction opposite to the conveyance direction) by the conveying section 30, the first rack 5 is conveyed to the transverse feed start position P3 (refer to FIG. 5). After that, as shown in FIG. 29, by moving the first rack 5 conveyed to the transverse feed start position P3 again in the X1 direction at a pitch of about 20 mm by the conveying section 30, the first rack 5 is re-conveyed to the sample supplying position 2a (3a).

Subsequently, after the first rack 5 has been completely moved from the transverse feed start position P3, the second rack 5 is conveyed to the transverse feed start position P3 by the fitting nails 237a (refer to FIG. 5) of the first rack moving mechanism 22, the state before the re-analysis (refer to FIG. 26) is obtained.

The conveying operation by the conveying section 30 will now be described in detail.

Figure 30:
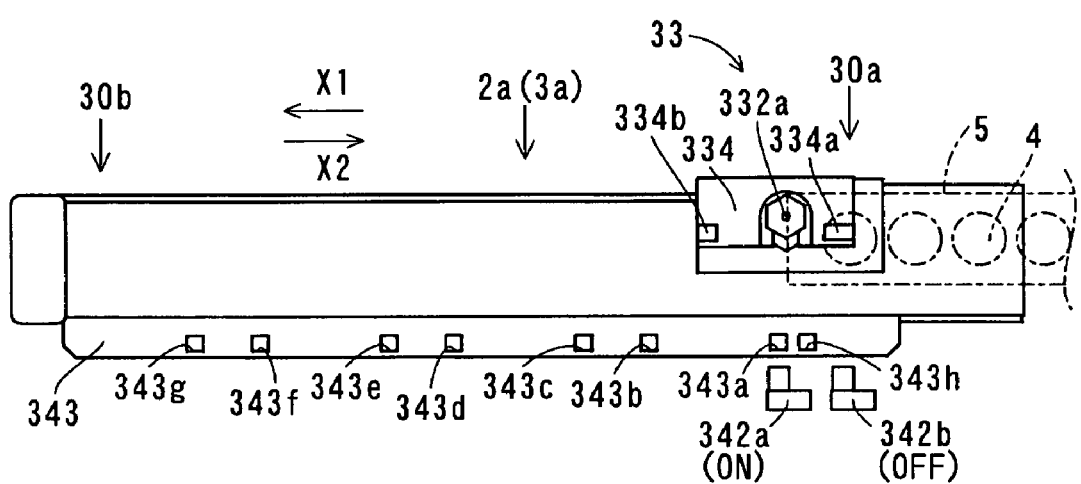
FIGS. 30 to 36 are schematic diagrams illustrating conveying operation of the conveying section in the conveying device according to the first embodiment shown in FIGS. 4 and 5.

First, as shown in FIG. 30, in the initial state, the rack conveyer 33 as a component of the conveying section 30 is in the initial position 30a. When the rack conveyer 33 moves at a pitch of about 20 mm in the X1 direction, the transmission sensors 342a and 342b of the rack conveyer 33 operate as follows.

Figure 31:
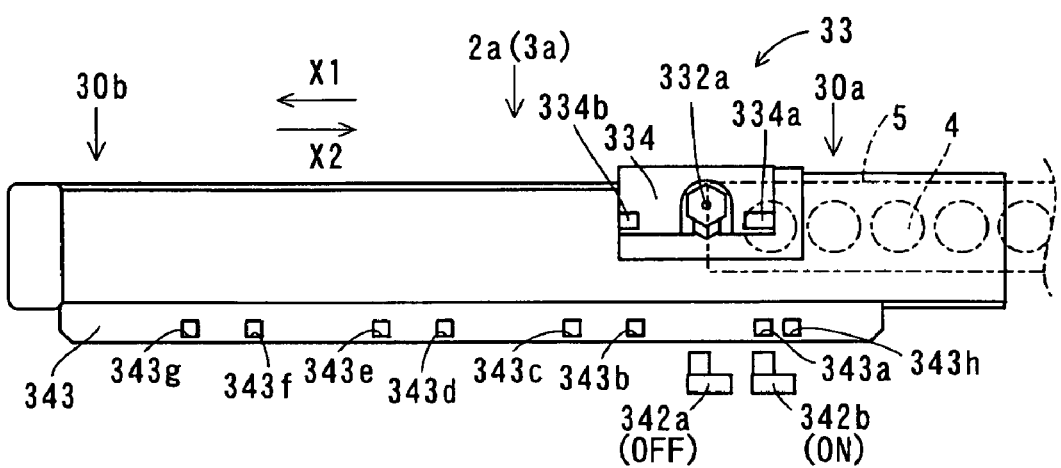
Figure 32:
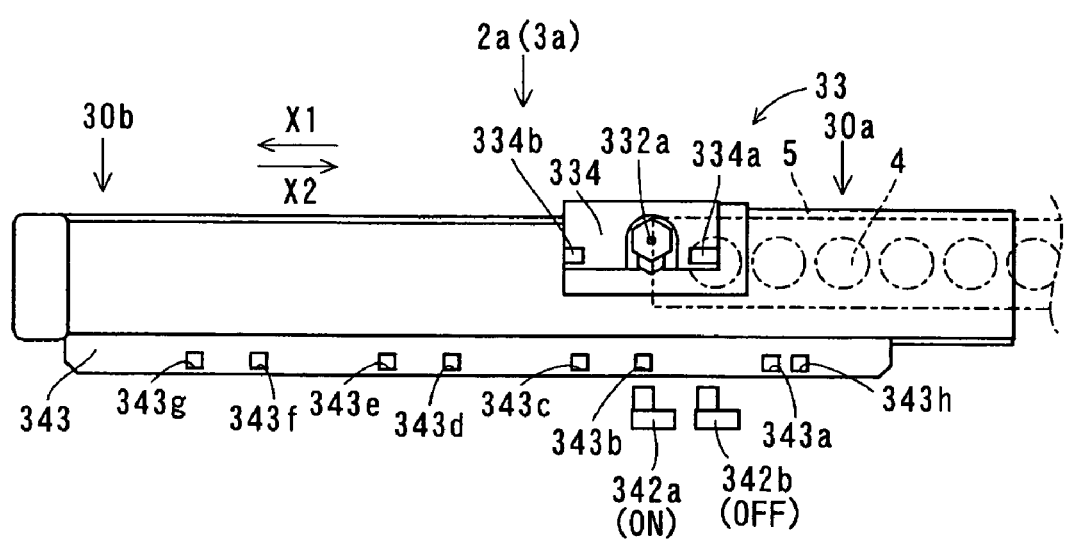
Figure 33:
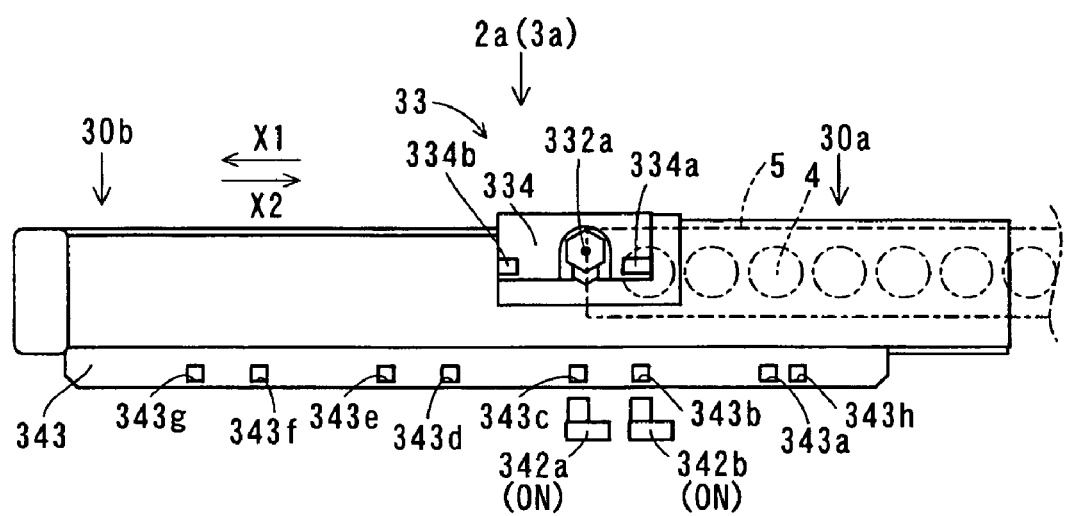

In the case where the rack conveyer 33 is in the initial state 30a as shown in FIG. 30, the transmission sensor 342a detects a light transmission (on) state, and the transmission sensor 342b detects a light shield (off) state. In the case where the rack conveyer 33 is moved from the initial position 30a only by about 20 mm (one pitch) as shown in FIG. 31, the transmission sensor 342a detects the off state, and the transmission sensor 342b detects the on state. In the case where the rack conveyer 33 is moved from the initial position 30a by about 40 mm (two pitches) as shown in FIG. 32, the transmission sensor 342a detects the on state, and the transmission sensor 342b detects the off state. In the case where the rack conveyer 33 is moved from the initial position 30a by about 60 mm (three pitches) as shown in FIG. 33, both of the transmission sensors 342a and 342b detect the on state.

As described above, each time the rack conveyer 33 is moved one pitch in the X1 direction, the combination of the transmission sensors 342a and 342b becomes one of the above-described patterns and always becomes a different pattern. Consequently, in the case where the position of the rack 5 is deviated by one pitch, the deviation can be easily detected. The three patterns are a first pattern in which the transmission sensor 342a detects the on state and the transmission sensor 342b detects the off state, a second pattern in which the transmission sensor 342a detects the off state and the transmission sensor 342b detects the on state, a third pattern in which both of the transmission sensors 342a and 342b detect the on state.

Figure 34:
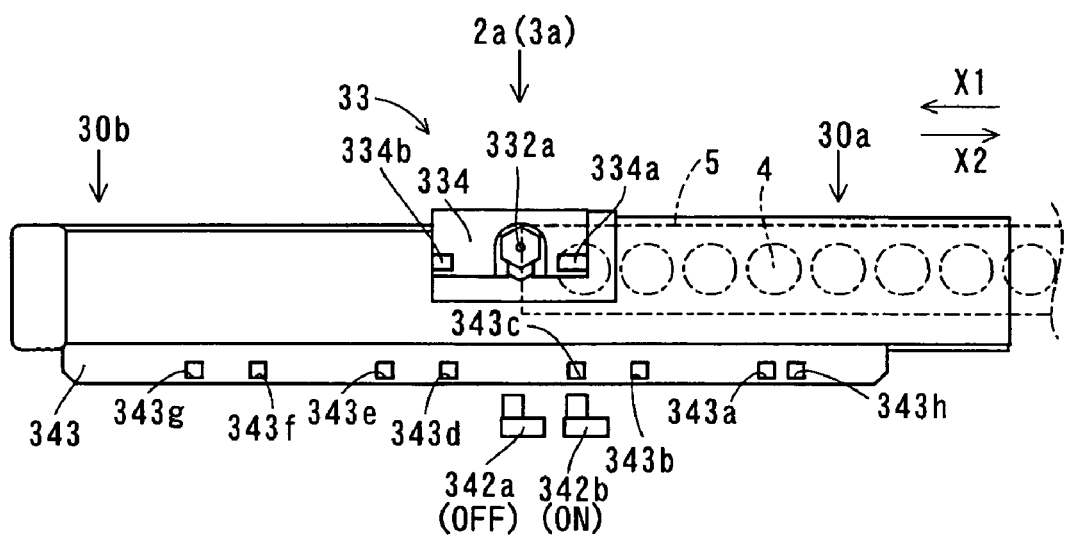
Figure 35:
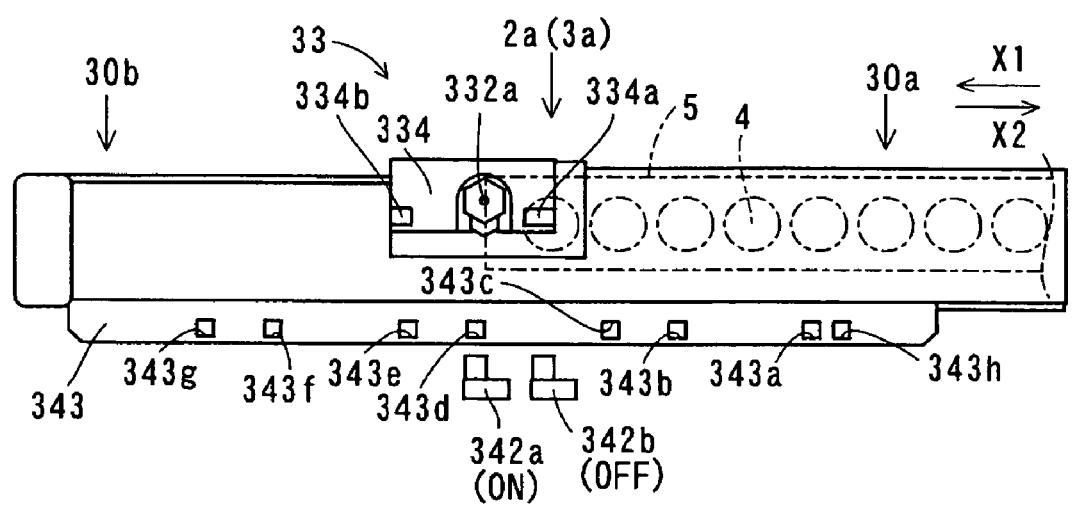

In the conveying section 30, when the first rack 5 is moved from the initial position 30a only by about 40 mm by the rack conveyer 33 (refer to FIG. 32), a barcode adhered to the first sample container 4 on the first rack 5 is read. As shown in FIG. 34, when the first rack 5 is moved from the initial position 30a only by about 80 mm (four pitches) by the rack conveyer 33, the sample in the first sample container 4 on the first rack 5 is stirred by the hand member 2b (3b) (refer to FIG. 1) of the first blood analyzer 2 (the second blood analyzer 3). As shown in FIG. 35, when the first rack 5 is moved from the initial position 30a only by about 100 mm (five pitches) by the rack conveyer 33, the sample in the first sample container 4 on the first rack 5 is supplied to the first blood analyzer 2 (the second blood analyzer 3) (refer to FIG. 1) by the hand member 2d (3b).

Figure 36:
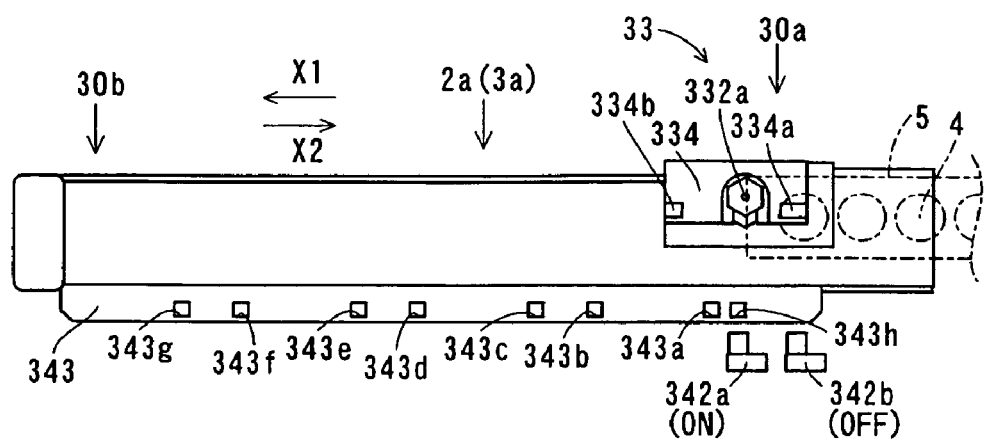

In the case where it is determined that a re-analysis is necessary on the sample in the sample container 4 held on the first rack 5, as shown in FIG. 36, the rack conveyer 33 is moved in the X2 direction. At this time, the rack conveyer 33 is moved in the X2 direction until the transmission sensor 342a of the rack conveyer 33 reaches the area corresponding to the detection hole 343h. The transmission sensors 342a and 342b detect the on state and the off state, respectively.

Figure 37:
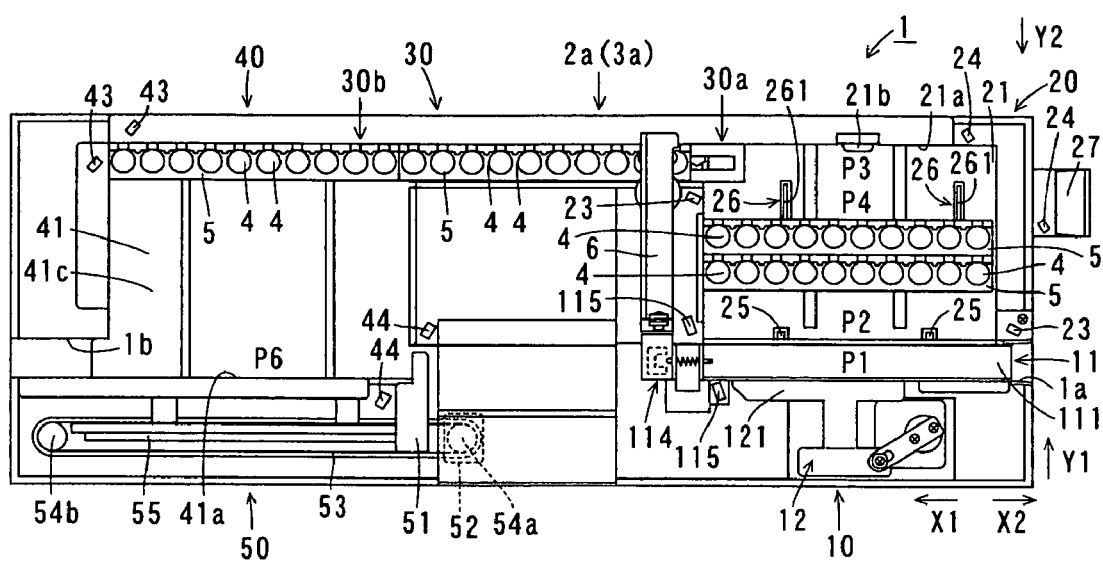
FIGS. 37 to 39 are schematic diagrams illustrating the conveying operation of the conveying device according to the first embodiment shown in FIGS. 4 and 5.

As shown in FIG. 37, by moving the first rack 5 in the X1 direction at a pitch of about 20 mm by the conveying section 30, the first rack 5 is conveyed to the ejection start position P5 (refer to FIG. 5). At this time, arrival at the ejection start position P5 of the first rack 5 is detected by the transmission sensor 43 in the carrying-out section 40.

Figure 38:
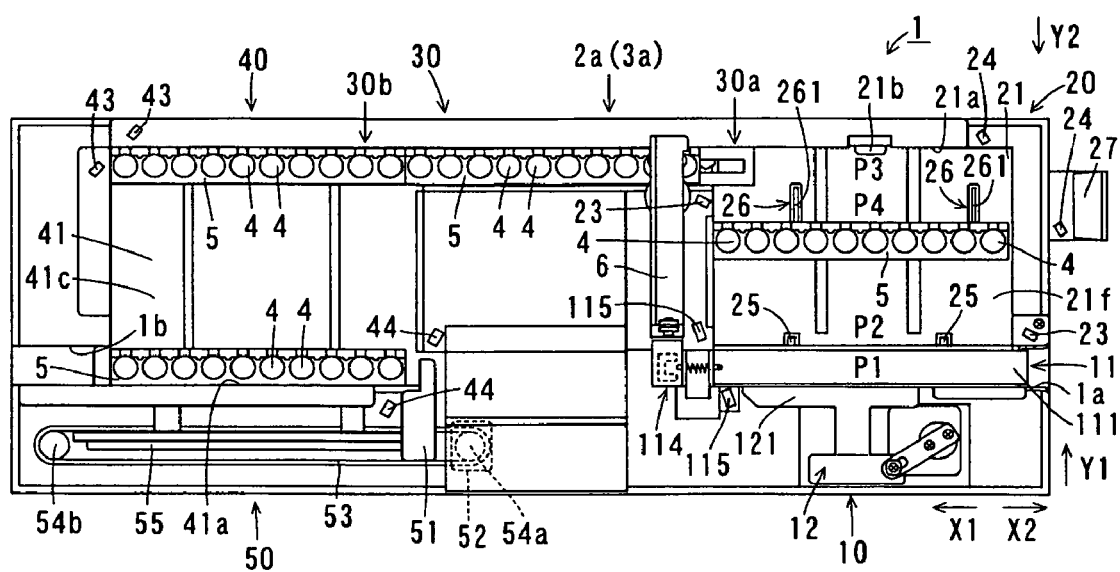

Next, as shown in FIG. 38, in the carrying-out section 40, by moving the first rack 5 conveyed to the ejection start position P5 (refer to FIG. 5) in the Y2 direction by the fitting members 421 (refer to FIG. 5) of the second rack moving mechanism 42, the first rack 5 is conveyed to the unloading start position P6 (refer to FIG. 5). At this time, arrival at the unloading start position P6 of the first rack 5 is detected by the transmission sensor 44 in the carrying-out section 40.

Figure 39:
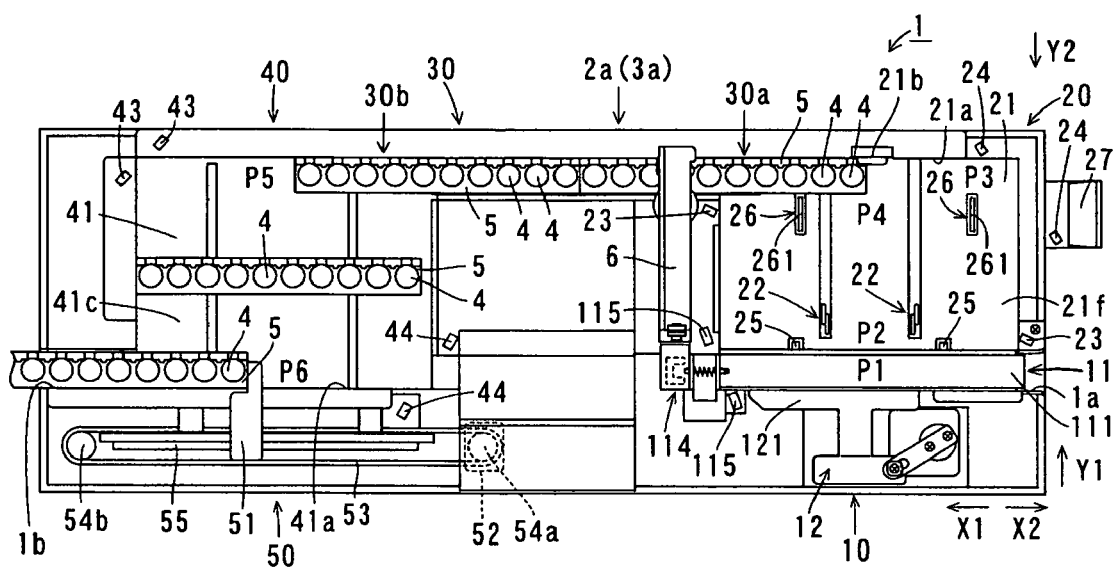

Finally, as shown in FIG. 39, in the unloading section 50, the first rack 5 is conveyed to the unloading start position P6 and, after that, the rack conveying member 51 is moved in the X1 direction. By the operation, the first rack 5 conveyed to the unloading start position P6 is moved in the X1 direction, so that the first rack 5 is unloaded from the outlet 1b.

Figure 48:
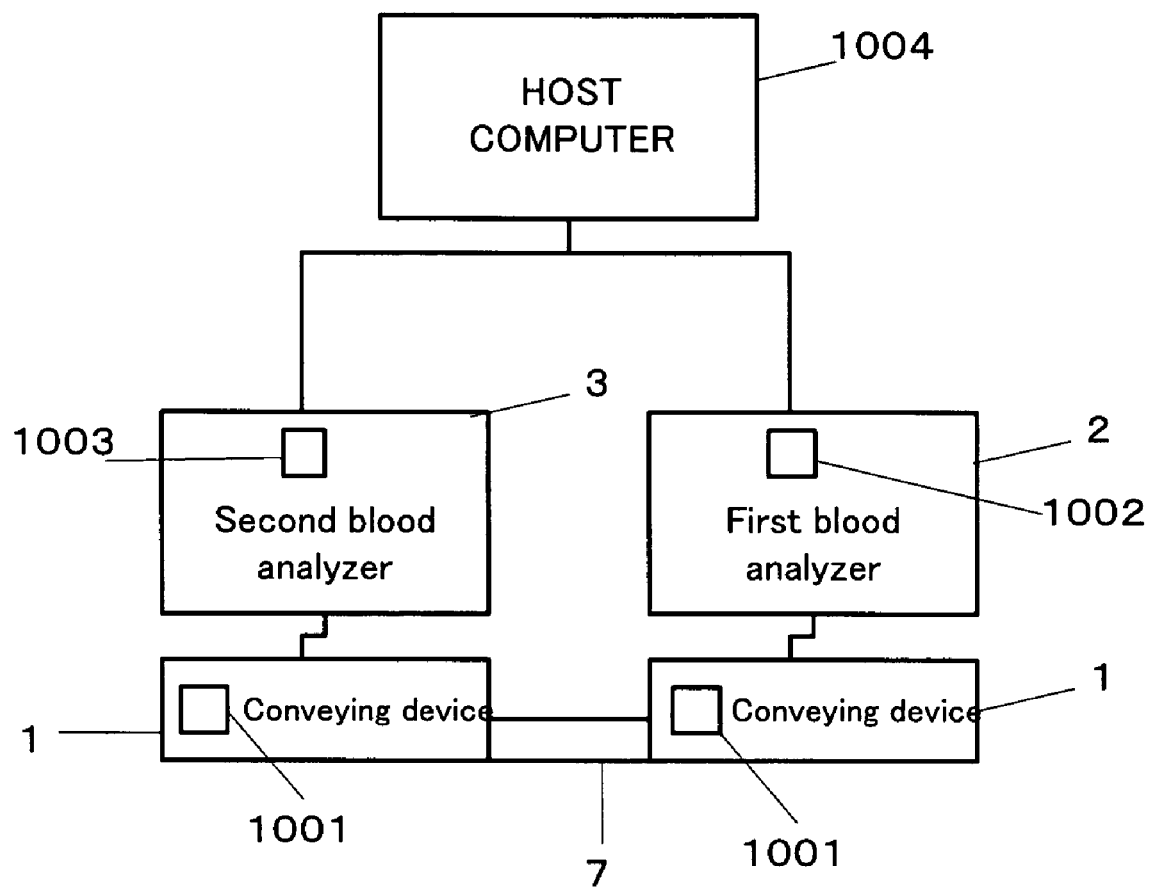
FIG. 48 is a block diagram showing a general configuration of a sample processing system according to the first embodiment of the invention.
Figure 49:
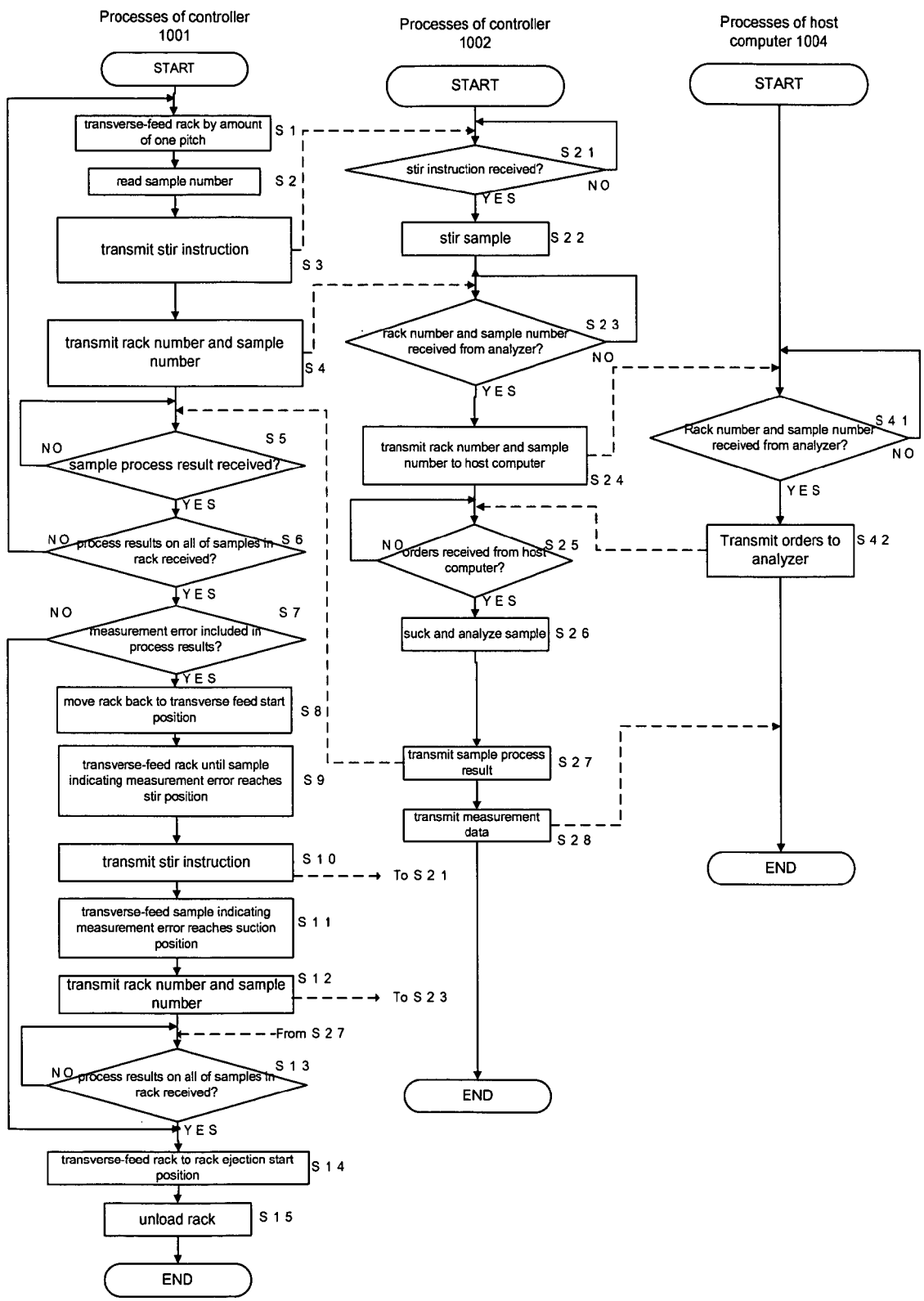
FIG. 49 is a flowchart showing processes executed by the sample processing system according to the first embodiment of the invention.

With reference to FIGS. 48 and 49, the sample processing system including the first and second blood analyzers 2 and 3 to each of which the conveying device 1 according to the first embodiment is connected will be further described. As shown in FIG. 48, the conveying device 1 has a controller 1001. The first blood analyzer 2 has a controller 1002, and the second blood analyzer 3 has a controller 1003. The first and second blood analyzers 2 and 3 are connected to a host computer 1004. The host computer 1004 is a computer including a CPU, a memory, a hard disk, and the like. On the hard disk of the host computer 1004, the rack number, sample number, and orders (information such as whether measurement is necessary or not and measurement items) on the sample are stored so as to be associated with each other. Each of the controllers 1001 to 1003 has a CPU, a memory, and the like, the controller 1001 is constructed so as to be able to perform communications with the controllers 1002 and 1003, and the controllers 1002 and 1003 can perform communications with the host computer 1004.

With reference to FIG. 49, part of processes executed by the controllers 1001 and 1002 and the host computer 1004 in order to convey a rack and process a sample will be described. FIG. 49 shows processes started when the rack 5 arrives at the transverse feed start position P3.

First, in step S1, the controller 1001 transverse-feeds the rack 5 only by one pitch (corresponding to the distance between two sample containers). At this time, one sample container reaches the position facing the barcode reader 2c, another sample container reaches the position (stir position) facing the hand member 2b, and further another sample container reaches a position (suction position) facing the hand member 2d. In step S2, the controller 1001 makes the barcode reader 2c read the barcode adhered to the sample container facing the barcode reader 2c. In step S3, the controller 1001 transmits a stir instruction to the controller 1002. In step S4, the controller 1001 transmits the number of the rack 5 (rack number) and the number of a barcode (sample number) adhered to a sample container in the suction position which are preliminarily read by the barcode reader 27 to the controller 1002. The sample number transmitted in step S4 was read by the barcode reader 2c when the sample container position in the suction position was in the position facing the barcode reader 2c. The processes in steps S2 to S4 are executed substantially at the same time. During the processes, the rack 5 is stopped and continuously stopped until stirring of the sample container in the stir position is finished and suction of the sample from the sample container in the suction position is completed.

On the other hand, the controller 1002 waits until the stir instruction is received from the controller 1001 (step S21) and, on receipt of the stir instruction, executes a process of stirring the sample with the hand member 2b in step S22. The controller 1002 waits until the rack number and the sample number are received from the controller 1001 in step S23 and, on receipt of the numbers, executes a process of transmitting the numbers to the host computer 1004 in step S24.

The host computer 1004 waits until the rack number and the sample number are received from the controller 1002 in step S41. On receipt of the numbers, in step S42, the host computer 1004 extracts the orders (information such as whether measurement is necessary or not and measurement items) of the sample on the basis of the numbers, and executes a process of transmitting the extracted orders to the controller 1002.

On the other hand, the controller 1002 waits until the orders are received from the host computer 1004 in step S25 and, on receipt of the orders, executes a process of taking the sample container 4 from the rack 5 with the hand member 2d, sucking the sample, and analyzing the sample in step S26.

After completion of analysis of the sample, the controller 1002 transmits the result of the sample process to the controller 1001 in step S27. In the case where the analysis of the sample is finished normally, the sample process result includes information indicating that the analysis of the sample has completed normally. When a re-analysis of the sample is necessary, the sample process result includes information indicative of a measurement error. In step S28, the controller 1002 transmits the sample measurement result (measurement data) to the host computer 1004.

On the other hand, the controller 1001 waits for reception of the sample process result in step S5. In step S6, the controller 1001 executes a process of determining whether the sample process results have been received on all of sample containers 4 held on the rack 5 or not. When it is determined that the sample process results on all of sample containers have not been received, the controller 1001 returns to step S1. The rack is transverse-fed by one pitch, the sample number of a new sample is read, a stir instruction is transmitted, and the rack number and the sample number are transmitted. In reality, irrespective of reception of the sample process result, when stirring of the sample is finished and suction of the sample is finished, transverse feed of one pitch of the rack is executed. However, to simplify the description, it is assumed that the reception of the sample process results relate to the beginning of transverse feed. When it is determined that the sample process results on all of the sample containers 4 have been received, the controller 1001 determines whether information indicative of a measurement error is included in the received sample process results or not ins step S7. In the case where information indicative of even one measurement error is included on all of the sample containers 4 held on the rack 5, the controller 1001 executes a process of moving the rack 5 back to the transverse feed start position P3 in step S8.

Next, in step S9, the controller 1001 transverse-feeds the rack 5 until the sample container 4 containing the sample indicating the measurement error arrives at the stir position. In step S10, the controller 1001 transmits the stir instruction to the controller 1002.

In step S11, the controller 1001 transverse-feeds the rack 5 until the sample container 4 containing the sample indicative of the measurement error reaches the suction position. In step S12, the controller 1001 transmits the rack number and the sample number to the controller 1002.

The controller 1001 executes the processes in steps S9 to S12 on all of samples indicative of a measurement error.

Further, the controller 1001 waits for receipt of the sample processing results in step S13. In the case where all of sample process results are received, in step S14, the controller 1001 executes a process of transverse-feeding the rack 5 to the ejection start position P5. In reality, irrespective of reception of the sample process results, when stir of the sample is finished and suction of the sample is finished, the rack is transversely fed. However, to simplify the description, the process as described above is assumed.

In step S15, the controller 1001 executes a process of conveying the rack 5 from the ejection start position P5 to the unloading start position P6.

In the case where no measurement error is included in the information on all of the sample containers 4 held on the rack 5 in step S7, the processes in steps S8 to S13 are not executed but the processes in step S14 and subsequent steps are executed.

Second Embodiment

Figure 40:
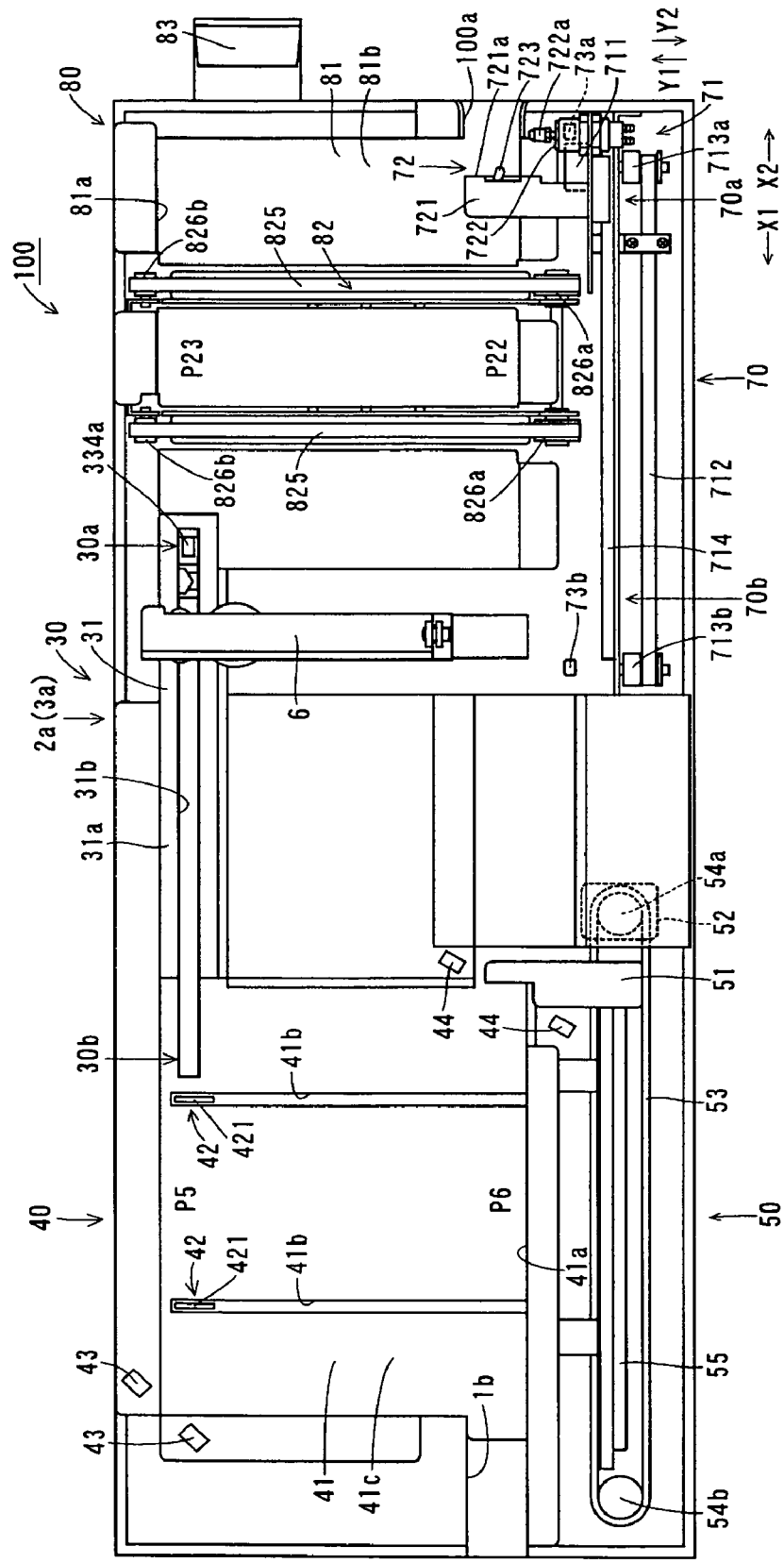
FIG. 40 is a plan view showing the structure of a conveying device according to a second embodiment of the invention.
Figure 41:
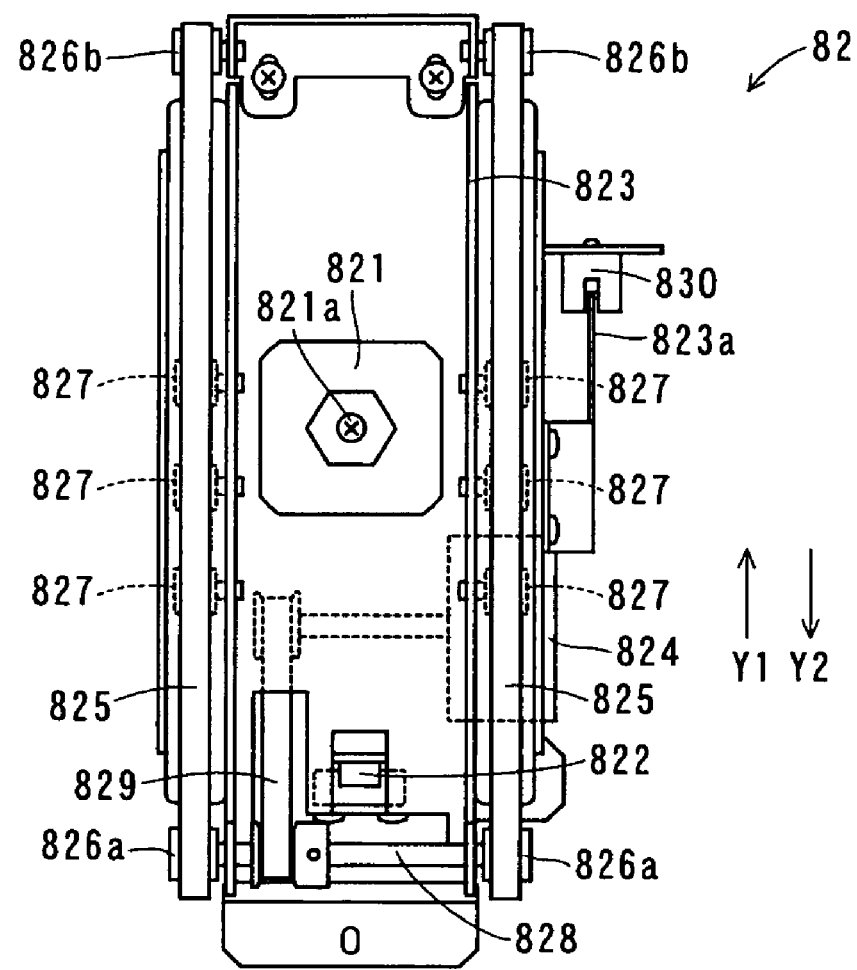
FIG. 41 is a plan view showing the structure of a first rack moving mechanism in the conveying device according to the second embodiment illustrated in FIG. 40.
Figure 42:
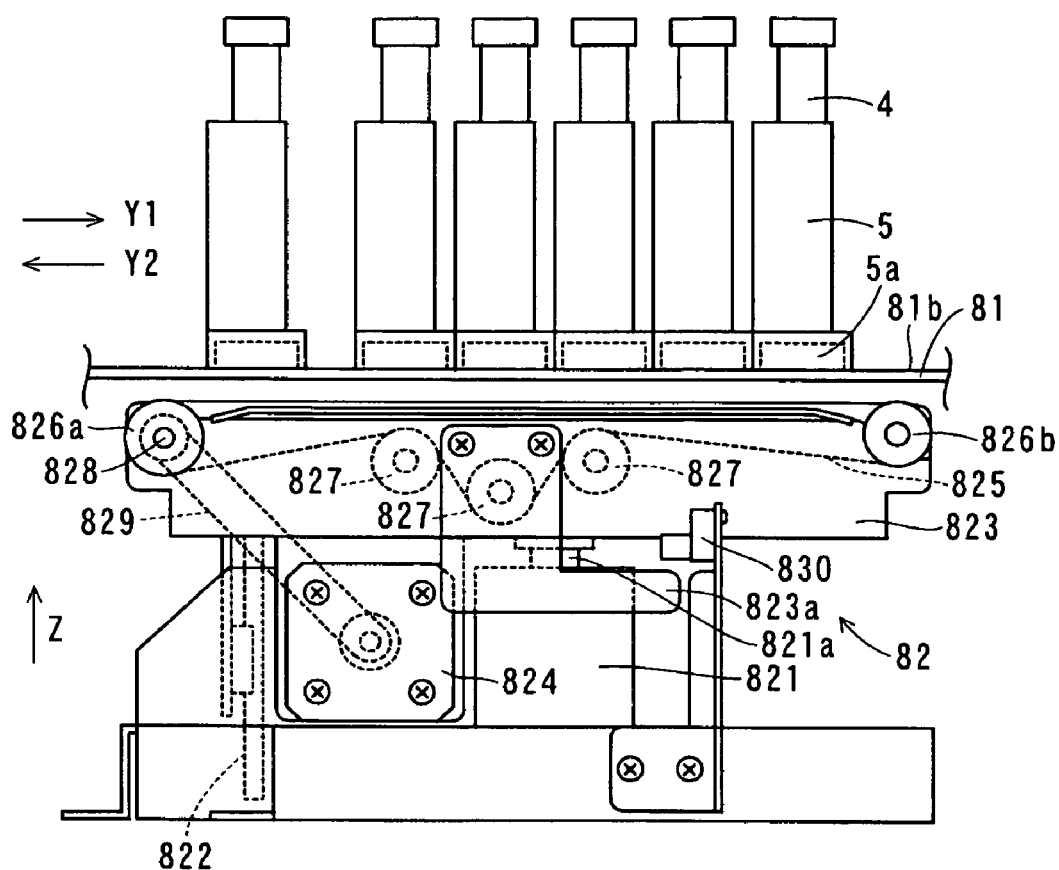
FIG. 42 is a side view of the first rack moving mechanism shown in FIG. 41.

FIG. 40 is a plan view showing the structure of a conveying device according to a second embodiment of the present invention. FIGS. 41 and 42 are detailed diagrams showing the structure of the conveying device according to the second embodiment illustrated in FIG. 40. With reference to FIG. 3 and FIGS. 40 to 42, the second embodiment will be described. Different from the foregoing first embodiment, conveyance of the rack 5 in a storing section 80 will be performed with a conveyance belt 825. The rack 5 conveyed by a conveying device 100 according to the second embodiment is the same as the rack 5 shown in FIGS. 2 and 3.

The conveying device 100 according to the second embodiment includes, as shown in FIG. 40, a rack receiver 70, the storing section 80, the conveying section 30, the carrying-out section 40, and the unloading section 50. The configurations of the conveying section 30, carrying-out section 40, and unloading section 50 in the conveying device 100 according to the second embodiment are similar to those of the conveying section 30, carrying-out section 40, and unloading section 50 in the conveying device 1 according to the first embodiment.

The rack receiver 70 in the conveying device 100 is provided to load the rack 5 introduced from an inlet 100a in the conveying device 100 to the storing section 80 side by moving the rack 5 in the X1 direction. The rack receiver 70 includes a driver 71, a rack conveyer 72, and transmission sensors 73a and 73b.

The driver 71 in the rack receiver 70 is provided to move the rack conveyer 72 in the X1 and X2 directions. The driver 71 is constructed by a motor 711, a drive belt 712, pulleys 713a and 713b, and a direct-drive guide 714. The motor 711 is coupled to the pulley 713a, and the drive belt 712 is attached to the pulleys 713a and 713b. Consequently, when the motor 711 is driven, the drive belt 712 is driven via the pulley 713a. The direct-drive guide 714 is disposed so as to extend in the X1 direction (X2 direction).

In the second embodiment, the rack conveyer 72 in the rack receiver 70 is provided to move the rack 5 introduced from the inlet 100a in the X1 direction and also has the function of a preventing member. A loading start position 70a in FIG. 40 is a position in which loading of the rack 5 by the rack conveyer 72 starts, and a loading end position 70b in FIG. 40 is a position in which loading of the rack 5 by the rack conveyer 72 is finished. The rack conveyer 72 includes a moving member 721, a solenoid 722, and a micro switch 723. The moving member 721 is coupled to the drive belt 712 and is also attached to the direct-drive guide 714. Consequently, when the drive belt 712 is driven in the X1 direction, the moving member 721 moves in the X1 directions along the direct-drive guide 714. The moving member 721 has a contact part 721a with which the rack 5 introduced from the inlet 100a comes into contact. The rack 5 is moved in the X1 direction by the rack conveyer 72 in a state where it is in contact with the contact part 721a of the moving member 721.

The micro switch 723 of the rack conveyer 72 is attached to the contact part 721a of the moving member 721. The micro switch 723 is disposed so that a switch part of the micro switch 723 is pressed by the rack 5 when the rack 5 comes into contact with the contact part 721a of the moving member 721. When the rack 5 comes into contact with the contact part 721a of the moving member 721, the micro switch 723 is switched from the on (off) state to the off (on) state, so that contact of the rack 5 with the contact part 721a can be detected.

The solenoid 722 in the rack conveyer 72 is attached to the moving member 721. The solenoid 722 is disposed so that a rod 722a of the solenoid 722 extends in the Y1 direction (Z direction) and is inserted in the slot 5c (refer to FIG. 3) in the rack 5 which is in contact with the contact part 721a of the moving member 721. Consequently, in the case where the rod 722a of the solenoid 722 is inserted in the slot 5c in the rack 5 and the rack conveyer 72 is moved in the X1 direction, the rod 722a of the solenoid 722 is fit in the slot 5c in the rack 5 so that the rack 5 is moved in the X1 direction.

The transmission sensors 73a and 73b in the rack receiver 70 are provided to detect the position of the rack conveyer 72 that moves in the X1 and X2 directions. Specifically, the transmission sensor 73a is provided to detect that the rack conveyer 72 has moved to the loading start position 70a. The transmission sensor 73a is disposed so as to detect that light is shielded by a detection piece (not shown) of the moving member 721 as a component of the rack conveyer 72 when the rack conveyer 72 is moved to the loading start position 70a. The transmission sensor 73b is provided to detect that the rack conveyer 72 has moved to the loading end position 70b. The transmission sensor 73b is disposed so as to detect that light is shielded by a detection piece (not shown) of the moving member 721 as a component of the rack conveyer 72 when the rack conveyer 72 is moved to the loading end position 70b. In the case where the rack conveyer 72 is moved to the loading start position 70a, the moving member 721 as a component of the rack conveyer 72 is positioned in a predetermined area above a storage plate 81 which will be described later. On the other hand, in the case where the rack conveyer 72 is moved to the loading end position 70b, the moving member 721 as a component of the rack conveyer 72 is positioned in an area deviated from the storage plate 81 which will be described later.

The storing section 80 of the conveying device 1 is provided to store the rack 5 conveyed from the inlet 100a to the sample supplying position 2a (3a). Further, in the second embodiment, the storing section 80 also has the function of re-storing the rack 5 moved in the direction opposite to the conveyance direction from the sample supplying position 2a (3a) in the case where a re-analysis is conducted. The storing section 80 includes the storage plate 81, a first rack moving mechanism 82, and a barcode reader 83.

The storage plate 81 in the storing section 80 is divided into three parts. The three divided storage plates 81 are disposed with predetermined intervals from each other. The storage plates 81 are disposed so as to provide an area through which the rack conveyer 72 (the contact part 721a of the moving member 721) of the rack receiver 70 which moves in the X1 (X2) direction passes. The storage plate 81 has a rack contact part 81a. The rack contact part 81a is provided on the side opposite to the rack receiver 70 side of the storage plate 81. The rack contact part 81a is formed by folding the storage plate 81 in the direction perpendicular to a mounting surface 81b. The area between the end on the rack receiver 70 side of the storage plate 21 and the rack contact part 81a is a storage area in which the rack 5 can be stored. In the storage plate 81, the area through which the rack conveyer 72 of the rack receiver 70 passes is a rack receive position P22 for receiving the rack 5 conveyed by the rack receiver 70. An area of the size of one rack 5 on the rack contact part 81a side of the storage plate 81 is a transverse feed start position P23 in which conveyance of the rack 5 by the conveying section 30 starts.

In the second embodiment, when the rack conveyer 72 (moving member 721) of the rack receiver 70 is moved to the loading start position 70a, storage in the rack receive position P22 of the rack 5 is regulated by the moving member 721. Specifically, when the rack conveyer 72 (moving member 721) of the rack receiver 70 is moved to the loading start position 70a, the rack conveyer 72 (moving member 721) functions as a preventing member for preventing the rack 5 from being stored in the rack receive position P22. When the rack conveyer 72 is moved to the loading end position 70b, since the rack conveyer 72 (moving member 721) is positioned in an area deviated from the storage plate 81, the rack conveyer 72 (moving member 721) does not function as a preventing member. The rack conveyer 72 starts loading of the rack 5 to the rack receive position P22 when there is an area in which at least one rack 5 can be stored other than the rack receive position P22 in the storing section 80.

In the second embodiment, the first rack moving mechanism 82 in the storing section 80 has, in addition to the function of moving the rack 5 stored on the mounting surface 81b of the storage plate 81 from the rack receive position P22 side to a transverse feed start position P23 side (Y1 direction), a function of moving the rack 5 in the direction opposite to the conveyance direction from the transverse feed start position P23 side to the rack receive side P22 (Y2 direction). The first rack moving mechanism 82 is disposed below the mounting surface 81b of the storage plate 81. The first rack moving mechanism 82 has, as shown in FIGS. 41 and 42, a cylinder 821, a direct-drive guide 822, a holder 823, a motor 824, two conveyance belts 825, a pair of pulleys 826a, a pair of pulleys 826b, a plurality of tension pulleys 827, a pulley shaft 828, a drive belt 829, and a transmission sensor 830. The cylinder 821 is disposed cylinder rod 821a to extend in a direction (Z direction) perpendicular to the mounting surface 81b of the storage plate 81, and the direct-drive guide 822 is disposed so as to extend in the Z direction. The holder 823 is attached to a cylinder rod 821a and the direct-drive guide 822. When the cylinder rod 821a extends in the Z direction, the holder 823 is moved in the extending direction (Z direction) of the direct-drive guide 822.

In the first rack moving mechanism 82, the motor 824, the pair of pulleys 826a, the pair of pulleys 826b, and the plurality of tension pulleys 827 are attached to the holder 823. The pulleys 826a as a pair are disposed so as to face each other with a predetermined interval, and the pulleys 826b as a pair are disposed so as to face each other with the same interval as that between the pulleys 826a. One of the two conveyance belts 825 is attached to the pulleys 826a and 862b on one side, and the other conveyance belt 825 is attached to the pulleys 826a and 826b on the other side. The conveyance belts 825 are disposed so as to project from the mounting surface 81b via areas corresponding to the internals among the three divided storage plates 81 when the holder 823 moves in the Z direction. Tension is applied to the conveyance belts 825 attached to the pulleys 826a and 826b by the plurality of tension pulleys 827.

In the first rack moving mechanism 82, the pulley shaft 828 is coupled to the pair of pulleys 826a, and the drive belt 829 is attached to the rotary shaft of the motor 824 and the pulley shaft 828. With the configuration, by driving of the motor 824, the conveyance belt 825 is driven via the drive belt 829, pulley shaft 828, and pulley 826a. In the case of driving the conveyance belt 825 in the Y1 direction (Y2 direction) in a state where it projects from the mounting surface 81b, the rack 5 comes into contact with the driving conveyance belt 825, thereby moving the rack 5 in the Y1 direction (Y2 direction).

The transmission sensor 830 of the first rack moving mechanism 82 is provided to detect that the conveyance belt 825 projects from the mounting surface 81b of the storage plate 81. The transmission sensor 830 is disposed so as to detect that light is shielded by a detection piece 823a attached to the holder 823 in the case where the conveyance belt 825 projects from the mounting surface 81b of the storage plate 81.

In the second embodiment, as described above, in the storing section 80, the first rack moving mechanism 82 for conveying the rack 5 received in the rack receive position P22 to the transverse feed start position P23 is constructed so as to be able to move the rack 5 in a direction opposite to the conveyance direction from the transverse feed start position P23 side to the rack receive position P22 side. Consequently, in a manner similar to the first embodiment, at the time of re-analyzing the sample in the sample container 4 held on the first rack 5 by the same analyzer, the second rack 5 already conveyed to the transverse feed start position P23 by the first rack moving mechanism 82 can be moved to an area other than the transverse feed start position P23 in the storing section 80. Thus, an area (transverse feed start position P23) for re-storing the first rack 5 can be assured in the storing section 80. As a result, in a manner similar to the first embodiment, at the time of re-analyzing the sample in the same analyzer, the rack 5 (sample) can be re-conveyed to the analyzer without requiring an operator.

In the second embodiment, by constructing the first rack moving mechanism 82 so as to include the conveyance belt 825 for moving the rack 5, by the conveyance belt 825 of the first rack moving mechanism 82, all of the racks 5 stored in the area other than the rack receive position P22 in the storing section 80 can be simultaneously moved from the transverse feed start position P23 side to the rack receive position P22 side in the direction opposite to the conveyance direction. In this case, by using the rack receive position P22 as an area in which storage of the rack 5 is regulated, at the time of re-analyzing the sample in the sample container 4 held on the first rack 5 by the same analyzer, the second rack 5 already conveyed to the transverse feed start position P23 can be moved together with the third or subsequent rack 5 to the area other than the transverse feed start position P23 in the storing section 80. Thus, the area for re-storing the first rack 5 (transverse feed start position P23) can be easily assured in the storing section 80.

In the second embodiment, in the case where the rack conveyer 72 of the rack receiver 70 is moved to the loading start position 70a of the rack 5, the rack conveyer 72 functions as the preventing member for regulating storage of the rack 5 in the rack receive position P22. Consequently, by moving the rack conveyer 72 to the loading start position 70a, storage of the rack 5 to the rack receiving position P22 can be easily regulated. By making the rack conveyer 72 function as the preventing member for regulating storage of the rack 5 into the rack receive position P22, it becomes unnecessary to separately provide a preventing member for regulating storage of the rack 5 to the rack receive position P22. Therefore, the number of parts can be reduced.

In the second embodiment, in the case where the rack conveyer 72 of the rack receiver 70 is moved in the direction opposite to the conveyance direction of the loading end position 70b of the rack 5, the rack conveyer 72 does not function as a preventing member. With the configuration, in the case where the rack 5 is moved in the direction opposite to the conveyance direction from the transverse feed start position P23 side to the rack receive position P22 side (in the case of re-processing the sample), by moving the rack conveyer 72 to the loading end position 70b, movement of the rack 5 from the transverse feed start position P23 side to the rack receive position P22 side is not disturbed by the rack conveyer 72.

In the second embodiment, in the case where an area in which at least one rack 5 can be stored exists other than the rack receive position P22 in the storing section 80, loading of the rack 5 to the rack receive position P22 by the rack conveyer 72 in the rack receiver 70 starts. With the configuration, even if the rack is conveyed to the rack receive position P22 (the area in which storage of the rack 5 is regulated), the rack 5 can be conveyed to an area other than the rack receive position P22 in the storing section 80. Thus, the rack 5 is not stored in the rack receive position P22.

FIGS. 43 to 47 are schematic diagram showing the conveying operation of the conveying device according to the second embodiment of the invention. With reference to FIG. 40 and FIGS. 43 to 47, the rack conveying operation of the conveying device 100 according to the second embodiment will now be described.

Figure 43:
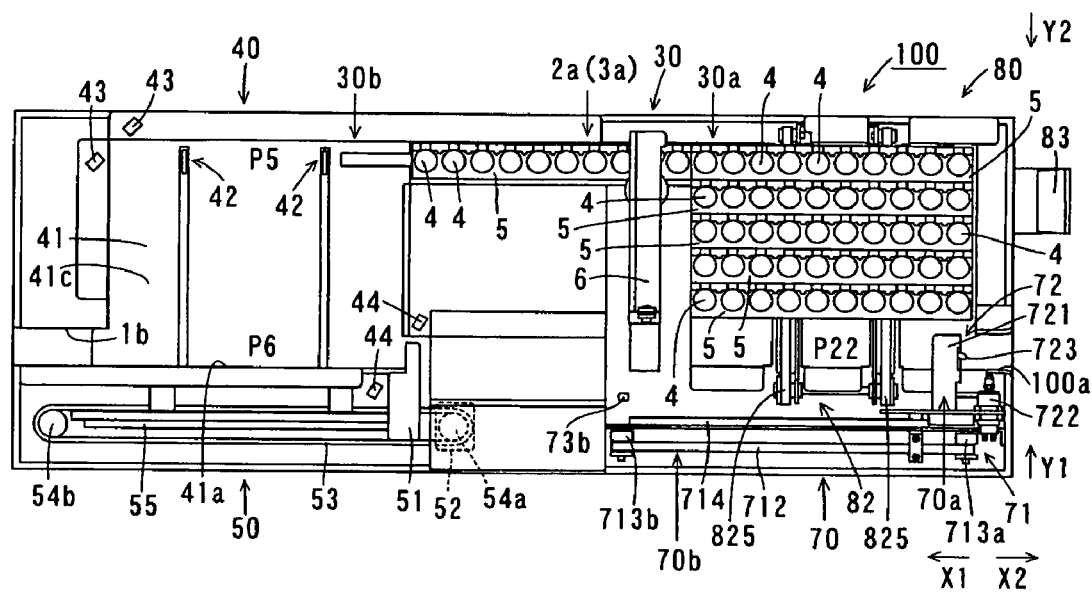
FIGS. 43 to 47 are schematic diagrams illustrating conveying operation of the conveying device according to the second embodiment of the invention.

First, as shown in FIG. 43, in the storing section 80, the first to sixth racks 5 sequentially conveyed from the rack receiver 70 are moved in the Y1 direction (conveyance direction) by the conveyance belts 825 of the first rack moving mechanism 82. By moving the first rack conveyed to the transverse feed start position P23 (refer to FIG. 40) in the X1 direction (conveyance direction) at a pitch of about 20 mm by the conveying section 30, the first rack 5 is conveyed to the sample supplying position 2a (3a). When the first rack 5 has been completely moved from the transverse feed start position P23, the second to sixth racks 5 are moved in the Y1 direction by the conveyance belt 825 of the first rack moving mechanism 82. Until the second rack 5 is conveyed to the transverse feed start position P23, the second to sixth racks 5 are moved in the Y1 direction. After that, the rack conveyer 72 in the rack receiver 70 is moved in the loading start position 70a (X2 direction).

As stated in FIG. 43, the operation performed in the case where it is determined that a re-analysis is necessary on the sample in the sample container 4 held on the first rack 5 will be described.

Figure 44:
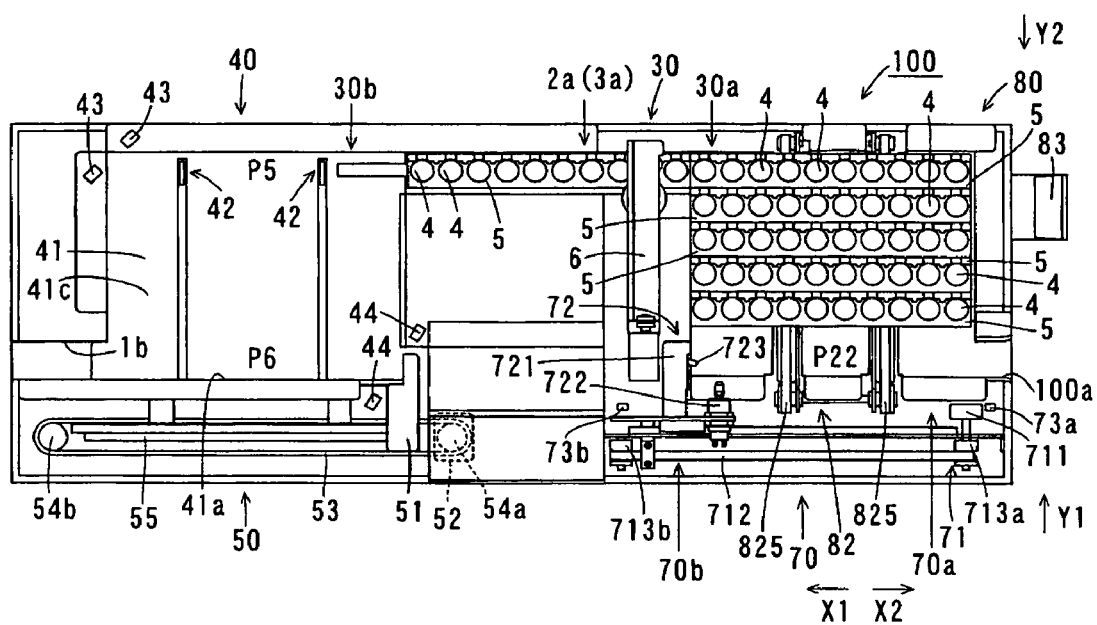

In the case where it is determined that a re-analysis is necessary on the sample in the sample container 4 held on the first rack 5, as shown in FIG. 44, first, the rack conveyer 72 is moved to the loading end position 70b (X1 direction) in the rack receiver 70.

Figure 45:
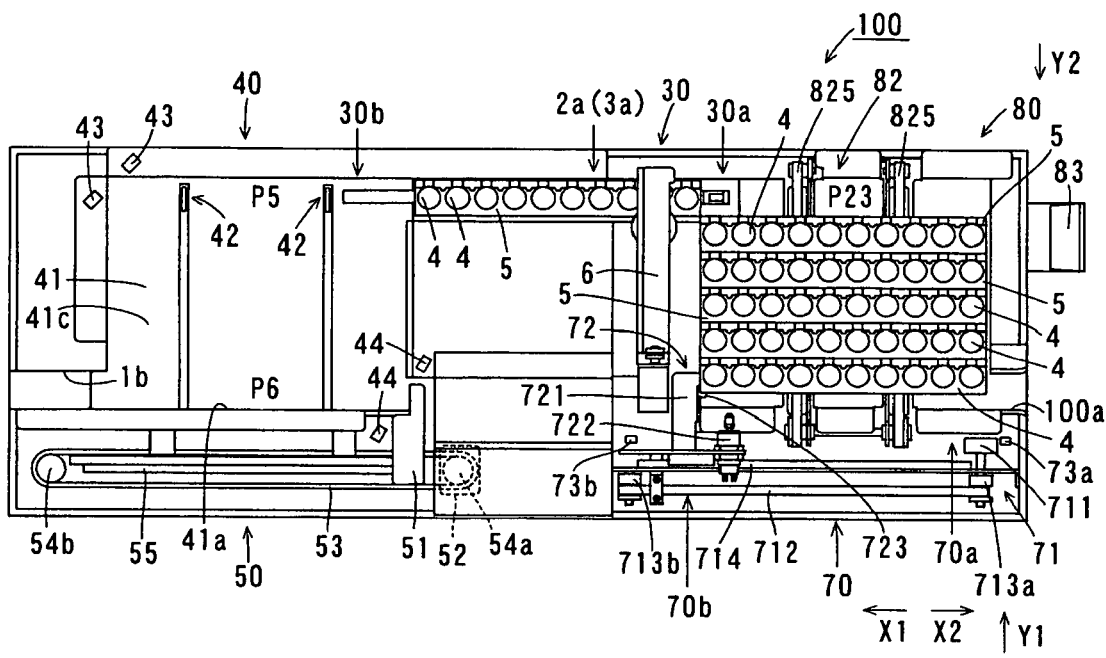

As shown in FIG. 45, the second to sixth racks 5 are moved in the Y2 direction as the direction opposite to the conveyance direction by the conveyance belt 825 of the first rack moving mechanism 82. Until the sixth rack 5 is conveyed to the rack receive position P22 (refer to FIG. 40), the second to sixth racks 5 are moved in the Y2 direction.

Figure 46:
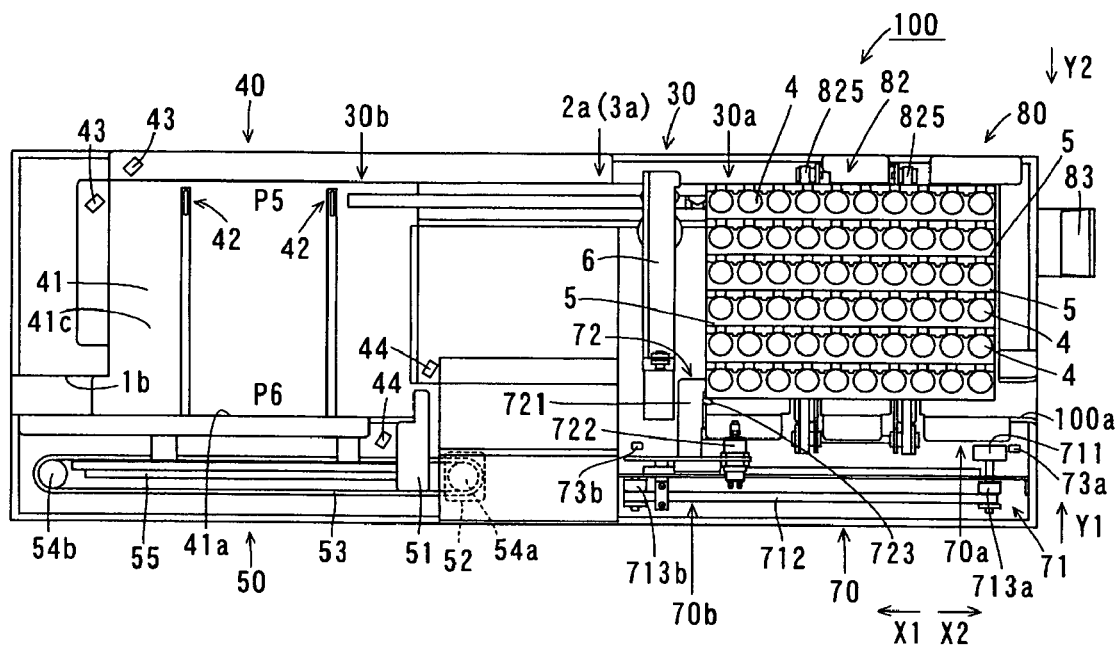
Figure 47:
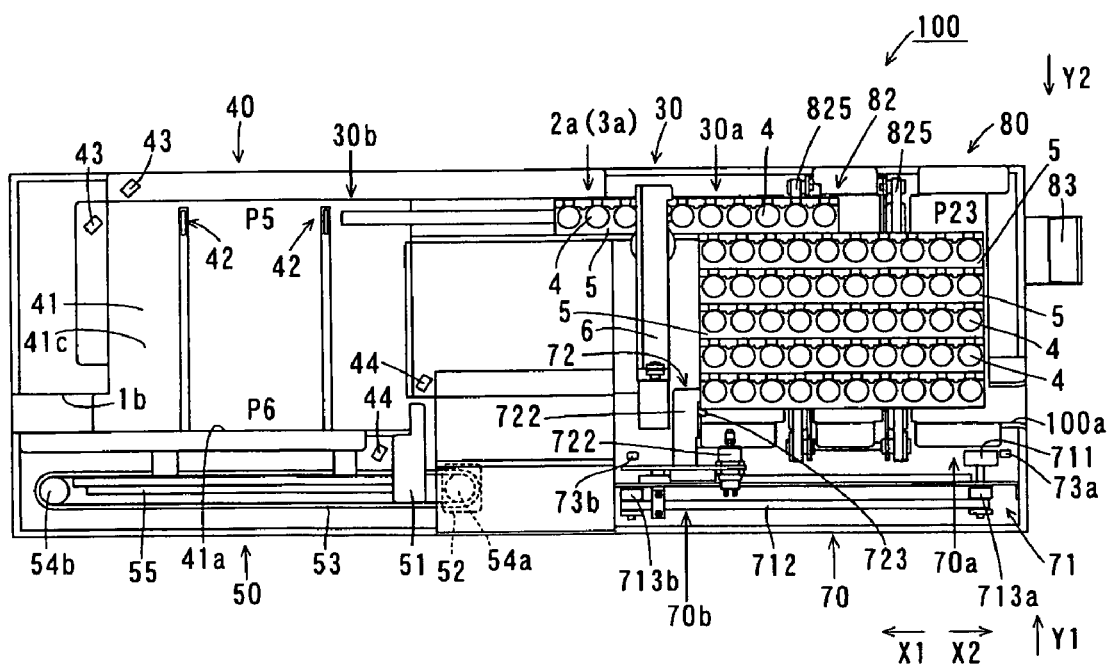

Next, as shown in FIG. 46, by moving the first rack 5 in the X2 direction as the direction opposite to the conveyance direction by the conveying section 30, the first rack 5 is moved to the transverse feed start position P23. After that, as shown in FIG. 47, the first rack 5 conveyed to the transverse feed start position P23 is moved again at a pitch of about 20 mm in the X1 direction by the conveying section 30, thereby re-conveying the first rack 5 to the sample supplying position 2a (3a). After the first rack has been completely conveyed from the transverse feed start position P23, the second rack 5 is conveyed to the transverse feed start position P23 by the conveyance belt 825 of the first rack moving mechanism 82, thereby resetting the state before the re-analysis (refer to FIG. 43).

The operations of conveying the rack 5 in the conveying section 30, carrying-out section 40, and unloading section 50 in the second embodiment are similar to those of the conveying section 30, carrying-out section 40, and unloading section 50 in the first embodiment, respectively.

It should be noted that the embodiments disclosed here are illustrative and not restrictive in all respects. The scope of the invention is indicated by the claims rather than by the foregoing description of the embodiments and all changes which come within the meaning and range of equivalency of the claims are intended to be embraced therein.

For example, in the first and second embodiments, the conveying device of the present invention is connected to the blood analyzer. The invention, however, is not limited to the embodiments. The conveying device of the invention may be connected to a sample processing device other than the blood analyzer.

Although a rack is conveyed by the first moving mechanism having the fitting nails or the conveyance belt in the storing section in the foregoing first and second embodiments, the invention is not limited to the above. A rack may be conveyed by a first moving mechanism other than the first moving mechanism having the fitting nails or the conveyance belt.

In the foregoing first and second embodiments, the controller 1001 provided for the conveying device 1 controls the operation of the conveying device 1 and performs communications with the first blood analyzer 1 or the second blood analyzer 2. Alternately, the sample processing system may have a computer having functions similar to those of the controller 1001, and the computer may be connected to the conveying device 1.

Although the sample processing system in which a plurality of conveying devices 1 are connected has been described in the first and second embodiments, the invention may be applied to a sample processing system in which a single or a plurality of analyzer(s) is/are connected to a single conveying device 1.

In the first and second embodiments, a space (reserve storage position P4) of one rack is assured in the storing section 20 or 80 and, in the case where a re-analysis is necessary on a sample, a rack is moved backward by using the space. The size of the space may be a size in which two or more racks can be mounted.

Although the conveying device 1 conveys the rack 5 in the Y2 direction and, after that, in the X1 direction in the first and second embodiments, the conveyance directions are not limited. By conveying the rack 5 only in the X1 direction, the rack 5 may be conveyed to the sample supplying position 2a or 3a.

What is claimed is:

1. A conveying device conveying a rack which holds a sample container, and supplying the sample container to a sample analyzer to analyze a sample in the sample container, comprising:

a storing section configured to store the rack and to supply the stored rack to a first position;

a conveying section configured to convey the rack from the first position to a supplying position to supply the sample container to the sample analyzer and to convey the rack from the supplying position to a second position; and a carry-out section configured to carry-out the rack from the second position and to store the carried-out rack;

wherein the conveying section comprises;

a fitting member configured to fit the rack, and a moving member configured to hold the fitting member, and being movable in a first direction from the first position to the second position through the supplying position and in a second direction from the second position to the first position through the supplying position, wherein the moving member is configured to convey the rack fitted by the fitting member from the first position to the supplying position, and to convey the rack fitted by the fitting member from the supplying position to the second position, and wherein the moving member is configured to convey the rack fitted by the fitting member in the second direction from the second position to the first position when the sample analyzer re-analyzes the sample in the sample container held by the rack.

2. The conveying device of claim 1, wherein the fitting member is configured to fit the supplied rack at the first position.

3. The conveying device of claim 1, wherein the moving member conveys the rack holding the sample container from the first position to the supplying position and to convey the rack holding the sample container supplied to the analyzer from the supplying position to the second position.

4. The conveying device of claim 1, wherein the moving member is configured to convey the rack a predetermined distance in the first direction so as to convey a sample container among a plurality of sample containers held in the rack to the sample supplying position one by one, the predetermined distance being equal to an interval of the adjacent sample containers held in the rack.

5. The conveying device of claim 1, wherein the storing section is configured to convey the stored rack in a third direction perpendicular to the first direction.

6. The conveying device of claim 1, wherein the carry-out section is configured to convey the carried-out rack from the second position in a fourth direction perpendicular to the first direction.

7. The conveying device of claim 1, wherein the sample analyzer aspirates a sample from the sample container which is conveyed to the supplying position by the moving member.

8. The conveying device of claim 1, wherein the rack holds a plurality of sample containers in a longitudinal direction of the rack.

9. The conveying device of claim 1, wherein the sample comprises blood.

10. A rack conveying system comprising:
a sample analyzer configured to analyze a sample in a sample container; and
a rack conveying device configured to convey the rack which holds the sample container and to supply the sample container to the sample analyzer,
wherein the rack conveying device comprises:
a storing section configured to store the rack and to supply the stored rack to a first position;
a conveying section configured to convey the rack from the first position to a supplying position to supply the sample container to the sample analyzer and to convey the rack from the supplying position to a second position; and
a carry-out section configured to carry-out the rack from the second position and to store the carried-out rack;
wherein the conveying section comprises;
a fitting member configured to fit the rack, and
a moving member configured to hold the fitting member, and being movable in a first direction from the first position to the second position through the supplying position and in a second direction from the second position to the first position through the supplying position,
wherein the moving member is configured to convey the rack fitted by the fitting member from the first position to the supplying position, and to convey the rack fitted by the fitting member from the supplying position to the second position,
wherein the moving member is configured to convey the rack fitted by the fitting member in the second direction from the second position to the first position when the sample analyzer re-analyzes the sample in the sample container held by the rack.

11. The conveying system of claim 10, wherein the fitting member is configured to fit the supplied rack at the first position.

12. The conveying system of claim 10, wherein the moving member conveys the rack holding the sample container from the first position to the supplying position and to convey the rack holding the sample container supplied to the analyzer from the supplying position to the second position.

13. The conveying system of claim 10, wherein the moving member is configured to convey the rack a predetermined distance in the first direction so as to convey a sample container among a plurality of sample containers held in the rack to the sample supplying position one by one, the predetermined distance being equal to an interval of the adjacent sample containers held in the rack.

14. The conveying system of claim 10, wherein the storing section is configured to convey the stored rack in a third direction perpendicular to the first direction.

15. The conveying system of claim 10, wherein the carry-out section is configured to convey the carried-out rack from the second position in a fourth direction perpendicular to the first direction.

16. The conveying system of claim 10, wherein the sample analyzer aspirates a sample from the sample container which is conveyed to the supplying position by the moving member.

17. The conveying system of claim 10, wherein the rack holds a plurality of sample containers in a longitudinal direction of the rack.

18. The conveying system of claim 10, wherein the sample comprises blood.

* * * * *